US008574583B2

(12) United States Patent
Kay et al.

(10) Patent No.: US 8,574,583 B2

(45) Date of Patent: Nov. 5, 2013

(54) AAV CAPSID LIBRARY AND AAV CAPSID PROTEINS

(75) Inventors: Mark Kay, Los Altos, CA (US); Dirk Grimm, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 2 days.

(21) Appl. No.: 13/297,110

(22) Filed: Nov. 15, 2011

(65) Prior Publication Data

US 2012/0066783 A1 Mar. 15, 2012

Related U.S. Application Data

(60) Division of application No. 12/538,791, filed on Aug. 10, 2009, now Pat. No. 8,067,014, which is a continuation of application No. 11/731,314, filed on Mar. 30, 2007, now Pat. No. 7,588,772.

(60) Provisional application No. 60/787,371, filed on Mar. 30, 2006.

(51) Int. Cl.

| | |
|---|---|
| ***A61K 39/42*** | (2006.01) |
| ***A61K 39/395*** | (2006.01) |
| ***A61K 49/00*** | (2006.01) |
| ***C12Q 1/70*** | (2006.01) |

(52) U.S. Cl.

USPC .................... 424/159.1; 424/130.1; 424/9.34; 424/9.1; 424/147.1; 435/5

(58) Field of Classification Search

None

See application file for complete search history.

(56) References Cited

U.S. PATENT DOCUMENTS

| | | | |
|---|---|---|---|
| 5,139,941 | A | 8/1992 | Muzyczka et al. |
| 5,436,146 | A | 7/1995 | Shenk et al. |
| 5,748,745 | A | 5/1998 | Bedini |
| 5,753,500 | A | 5/1998 | Shenk et al. |
| 5,773,289 | A | 6/1998 | Samulski et al. |
| 5,863,541 | A | 1/1999 | Samulski et al. |
| 5,869,305 | A | 2/1999 | Samulski et al. |
| 5,993,800 | A | 11/1999 | Linsley et al. |
| 6,024,059 | A | 2/2000 | Kamimaru et al. |
| 6,040,183 | A | 3/2000 | Ferrari et al. |
| 6,057,152 | A | 5/2000 | Samulski et al. |
| 6,093,570 | A | 7/2000 | Ferrari et al. |
| 6,268,213 | B1 | 7/2001 | Samulski et al. |
| 6,410,300 | B1 | 6/2002 | Samulski et al. |
| 6,458,587 | B2 | 10/2002 | Ferrari et al. |
| 6,489,162 | B1 | 12/2002 | Shenk et al. |
| 6,491,907 | B1 | 12/2002 | Rabinowitz et al. |
| 6,548,286 | B1 | 4/2003 | Samulski et al. |
| 6,627,617 | B1 | 9/2003 | Samulski et al. |
| 6,670,176 | B1 | 12/2003 | Samulski et al. |
| 6,703,237 | B2 | 3/2004 | Samulski et al. |
| 6,936,243 | B2 | 8/2005 | Snyder et al. |
| 6,943,012 | B2 | 9/2005 | Ehrhardt et al. |
| 6,951,753 | B2 | 10/2005 | Shenk et al. |
| 6,951,758 | B2 | 10/2005 | Ferrari et al. |
| 7,060,497 | B2 | 6/2006 | Nakai et al. |
| 7,148,341 | B2 | 12/2006 | Kleinschmidt et al. |
| 7,172,893 | B2 | 2/2007 | Rabinowitz et al. |
| 7,198,951 | B2 | 4/2007 | Gao et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,465,583 | B2 | 12/2008 | Samulski et al. |
| 7,588,772 | B2 | 9/2009 | Kay et al. |
| 7,790,154 | B2 | 9/2010 | Samulski et al. |
| 7,867,484 | B2 | 1/2011 | Samulski et al. |
| 7,892,809 | B2 | 2/2011 | Bowles et al. |
| 7,923,436 | B2 | 4/2011 | Monahan et al. |
| 2002/0045264 | A1 | 4/2002 | During et al. |
| 2002/0058341 | A1 | 5/2002 | Nakai et al. |
| 2002/0076798 | A1 | 6/2002 | Miao et al. |
| 2002/0076801 | A1 | 6/2002 | Kleinschmidt et al. |
| 2002/0151509 | A1 | 10/2002 | Snyder et al. |
| 2002/0192823 | A1 | 12/2002 | Bartlett |
| 2003/0022378 | A1 | 1/2003 | Ehrhardt et al. |
| 2003/0138772 | A1 | 7/2003 | Gao et al. |
| 2004/0009151 | A1 | 1/2004 | Kay et al. |
| 2004/0077576 | A1 | 4/2004 | Kay et al. |
| 2004/0180440 | A1 | 9/2004 | Zolotukhin |
| 2004/0203133 | A1 | 10/2004 | Ehrhardt et al. |
| 2004/0209364 | A1 | 10/2004 | Grimm et al. |

(Continued)

FOREIGN PATENT DOCUMENTS

| | | |
|---|---|---|
| WO | WO 03/042397 | 5/2003 |
| WO | WO 03/052052 | 6/2003 |
| WO | WO 2005/033321 | 4/2005 |
| WO | WO 2005/072364 | 8/2005 |

OTHER PUBLICATIONS

Maheshri et al., Directed evolution of adeno-associated virus yields enhanced gene delivery vectors, 2006, Nature Biotechnology, vol. 24, No. 2, pp. 198-204.*

Lochrie et al., Mutations on the External Surfaces of Adeno-Associated Virus Type 2 Capsids That Affect Transduction and Neutralization, (Jan. 2006), Journal of Virology, vol. 80, No. 2, pp. 821-834.*

Appendix I—Sequence alignment conducted on Apr. 2, 2008.

Appendix 2—Sequence alignment conducted on Apr. 2, 2008.

Bowles et al., "Marker rescue of adeno-associated virus (AAV) capsid mutants: a novel approach for chimeric AAV production", Journal of Virology, vol. 77, No. 1, pp. 423-432 (2003).

Chen et al., "Molecular characterization of adeno-associated viruses infecting children", Journal of Virology, vol. 29, No. 23, pp. 14781-14792 (2005).

(Continued)

*Primary Examiner* — Benjamin P Blumel

(74) *Attorney, Agent, or Firm* — Judy M. Mohr; Susan J. Myers Fitch; McDermott Will & Emery LLP

(57) ABSTRACT

Recombinant adeno-associated viral (AAV) capsid proteins are provided. Methods for generating a library of recombinant adeno-associated viral capsid proteins are also provided.

6 Claims, 9 Drawing Sheets

(56) References Cited

U.S. PATENT DOCUMENTS

| | | | |
|---|---|---|---|
| 2004/0214329 | A1 | 10/2004 | Kay et al. |
| 2004/0235174 | A1 | 11/2004 | Grimm et al. |
| 2005/0014262 | A1 | 1/2005 | Gao et al. |
| 2006/0188482 | A1 | 8/2006 | Kay et al. |
| 2006/0189561 | A1 | 8/2006 | Roelvink et al. |
| 2006/0223778 | A1 | 10/2006 | Kay et al. |
| 2007/0036760 | A1 | 2/2007 | Wilson et al. |

OTHER PUBLICATIONS

Choi et al., "AAV hybrid serotypes: improved vectors for gene delivery", Current Gene Therapy, vol. 5, No. 3, pp. 299-310 (2005).

Database UniProt [Online] "Capsid Protein VP1", retrieved from EBI Accesion No. Uniprot:Q670R0, Database Accession No. Q670R0 (Oct. 11, 2004).

Gao et al., Genbank Accesion # AF513852, Sep. 5, 2002.

Gao et al., Genbank Accession # AAS99284.1, Jun. 24, 2004.

Gao et al., Genbank Accession # AY530579, Jun. 24, 2004.

Gao et al., "Clades of Adeno-Associated Viruses Are Widely Disseminated in Human Tissues", Journal of Virology, vol. 78, No. 21, pp. 6381-6388 (2004).

Grimm et al., "Liver transduction with recombinant adeno-associated virus is primarily restricted by capsid serotype not vector genotype", Journal of Virology, vol. 80, No. 1, pp. 426-439.

International Search Report and Written Opinion for PCT/US2007/008314, Search report dated May 16, 2008, 17 pages.

Ruffing et al., "Mutations in the carboxy terminus of adeno-associated virus 2 capsid proteins affect viral infectivity: lack of an RGD integrin-binding motif", Journal of General Virology, vol. 75, pp. 3385-3392 (1994).

Ruffing et al., Genbank Accession # AAC03780, Feb. 24, 1998.

Ruffing et al., Genbank Accession # AF043303, Feb. 24, 1998.

Wu et al., "Mutational analysis of the adeno-associated virus type 2 (AAV2) capsid gene and construction of AAV2 vectors with altered tropism", Journal of Virology, vol. 74, No. 18, pp. 8635-8647 (2000).

Kay, "State-of-the-art gene-based therapies: the road ahead", Nature Reviews Genetics, Advance Online Publication, doi:10.1038/nrg2971, 13 pgs., published online Apr. 6, 2011.

Yirrell et al., "Comparison of the continous cell line 293 with human embryo kidney cells and human embryo fibroblast cells for the cultivation of ocular viruses", J. Clinical Pathology, vol. 36, pp. 996-999 (1983).

Zhou et al., "Properties of HERG channels stably expressed in HEK 293 cells studied at physiological temperature", Biophysical J., vol. 74, pp. 230-241 (1998).

* cited by examiner

```
AAV-DJ:       MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEF  100
AAV-2:    1   MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEF  100
AAV-8:    1   MAADGYLPDWLEDNLSEGIREWWALKPGAPKPKANQQKQDDDSRGLVLPGYKYLGPFNGLDKGEPVNEADAAALEHDKAYDRQLQAGDNPYLRYNHADAEF  100
AAV-9:    1   MAADGYLPDWLEDNLSEGIREWWALKPGAPQPKANQQHQDWARGLVLPGYKYLGPFNGLDKGEPVNAADAAALEHDKAYDQQLKAGDNPYLKYNHADAEF  100

AAV-DJ:       QERLKEDTSFGGNLGRAVFQAKKRLLEPLGLVEEAAKTAPGKKRPVEISPVE-PDSSSGTGKAGQQPARKRLNFGQTGDADSVPDPQPIGEPPAAPSGVG  199
AAV-2:   101  QERLKEDTSFGGNLGRAVFQAKKRLLEPLGLVEEAAKTAPGKKRPVEHSPVE-PDSSSGTGKAGQQPARKRLNFGQTGDADSVPDPQPLGQPPAAPSGLG  199
AAV-8:   101  QERLQEDTSFGGNLGRAVFQAKKRVLEPLGLVEEPVKTAPGKKRPVEPSPQRSPDSSTGIGKKGQQPARKRLNFGQTGDSESVPDPQPLGEPPAAPSGVG  200
AAV-9:   101  QERLKEDTSFGGNLGRAVFQAKKRVLEPLGLVEEGAKTAPGKKRPVEQSPQE-PDSSAGIGKSGAQPAKKRLNFGQTGDTESVPDPQPIGEPPAAPSGVG  199

AAV-DJ:       SLTMAAGGGAPMADNNEGADGVGNSSGNWHCDSTWMGDRVITTSTRTWALPTYNNHLYKQISNSTSGGSSNDNAYFGYSTPWGYFDFNRFHCHFSPRDWQ  297
AAV-2:   200  TNTMATGSGAPMADNNEGADGVGNSSGNWHCDSTWMGDRVITTSTRTWALPTYNNHLYKQISSQSGASNDNHYFGYSTPWGYFDFNRFHCHFSPRDWQ   300
AAV-8:   201  PNTMAAGGGAPMADNNEGADGVGSSSGNWHCDSTWLGDRVITTSTNGATNDNTYFGYSTPWGYFDFNRFHCHFSPRDWQ   299
AAV-9:   200  SLTMASGGGAPVADNNEGADGVGSSSGNWHCDSTWLGDRVITTSTRTWALPTYNNHLYKQISNGTSGGATNDNTYFGYSTPWGYFDFNRFHCHFSPRDWQ  299

                                                                      ┌──────────2──────────┐          ┌──────1──────┐

AAV-DJ:       RLINNNWGFRPKRLSFKLFNIQVKEVTQNEGTKTIANNLTSTIQVFTDSEYQLPYVLGSAHQGCLPPFPADVFMIPQYGYLTLNNGSQAVGRSSFYCLEY  397
AAV-2:   298  RLINNNWGFRPKRLNFKLFNIQVKEVTQNDGTTTIANNLTSTVQVFTDSEYQLPYVLGSAHQGCLPPFPADVFMVPQYGYLTLNNGSQAVGRSSFYCLEY  400
AAV-8:   301  RLINNNWGFRPKKLSFKLFNIQVKEVTQNDGTTTIANNLTSTIQVFTDSEYQLPYVLGSAHQGCLPPFPADVFMIPQYGYLTLNDGSQAVGRSSFYCLEY  400
AAV-9:   300  RLINNNWGFRPKRLNFKLFNIQVKEVTDNNGVKTIANNLTSTIQVFSDSEYQLPYVLGSAHQGCLPPFPADVFMIPQYGYLTLNDGSQAVGRSSFYCLEY  399

                                                                ┌──3──┐
```

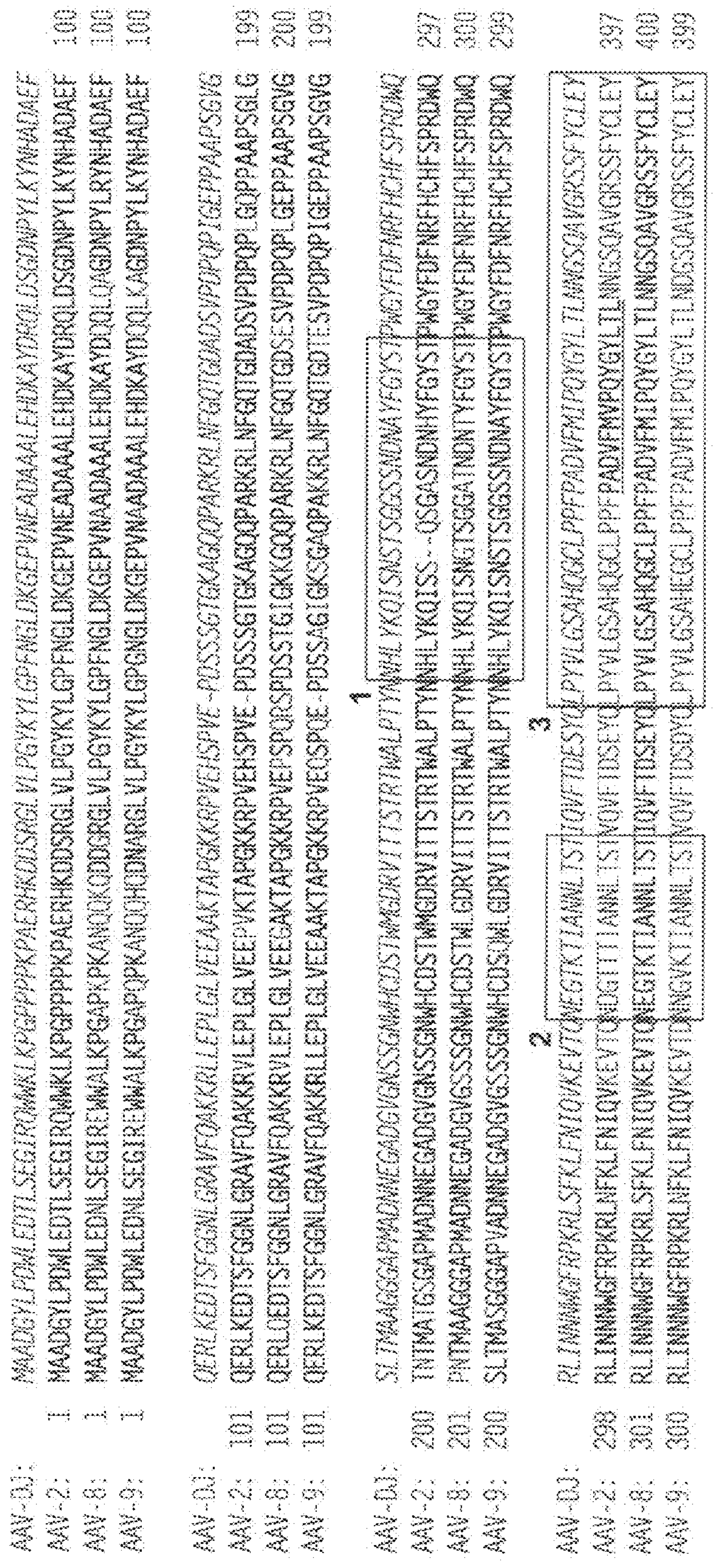

FIG. 1A

```
                 4
AAV-DJ:      FPSQMLKTGNNFQFTYTFEDVPFHSSYAHSQSLDRLMNPLIDQYLYYLSRTQTTGGTTNTQTLGFSQGGXNTMANQAKNWLPGPCYRQQRVSKTSADNNN
AAV-2:  398  FPSQMLRTGNNFTFSYTFEDVPFHSSYAHSQSLDRLMNPLIDQYLYYLSRTNTPSGTTTQSRLQFSQAGASDIRDQSRNWLPGPCYRQQRVSKTSADNNN  497
AAV-8:  401  FPSQMLRTGNNFQFTYTFEDVPFHSSYAHSQSLDRLMNPLIDQYLYYLSRTQTTGGTANTQTLGFSQGGPNTMANQAKNWLPGPCYRQQRVSTTTGQNNN  500
AAV-9:  400  FPSQMLRTGNNFQFSYEFENVPFHSSYAHSQSLDRLMNPLIDQYLYYLSKTINGSGQNQQ-TLKFSVAGPSNMAVQGRNYIPGPSYRQQRVSTTVTQNNN  499

AAV-DJ:      SEYSWTGATKYHLNGRDSLVNPGPAMASHKDDEEKFFPQSGVLIFGKQGSEKTNVDIEKVMITDEEEIRTTNPVATEQYGSVSTNLQRGNRQAATADVNT
AAV-2:  498  SEYSWTGATKYHLNGRDSLVNPGPAMASHKDDEEKFFPQSGVLIFGKQGSEKTNVDIEKVMITDEEEIRTTNPVATEQYGSVSTNLQRGNRQAATADVNT  597
AAV-8:  501  SNFAWTAGTKYHLNGRNSLANPGIAMATHKDDEERFFPSNGILIFGKQNAARDNADYSDVMLTSEEEIKTTNPVATEEYGIVADNLQQQNTAPQIGTVNS  600
AAV-9:  500  SEFAWPGASSWALNGRNSLMNPGPAMASHKEGEDRFFPLSGSLIFGKQGTGRDNVDADKVMITNEEEIKTTNPVATESYGQVATNHQSAQAQAQTGWVQN  599

                                                          5
AAV-DJ:      QGVLPGMVWQDRDVYLQGPIWAKIPHTDGHFHPSPLMGGFGLKHPPPQILIKNTPVPADPPTTFNQSKLNSFITQYSTGQVSVEIEWELQKENSKRWNPE
AAV-2:  598  QGVLPGMVWQDRDVYLQGPIWAKIPHTDGHFHPSPLMGGFGLKHPPPQILIKNTPVPANPSTTFSAAKFASFITQYSTGQVSVEIEWELQKENSKRWNPE  697
AAV-8:  601  QGALPGMVWQNRDVYLQGPIWAKIPHTDGNFHPSPLMGGFGLKHPPPQILIKNTPVPADPPTTFNQSKLNSFITQYSTGQVSVEIEWELQKENSKRWNPE  700
AAV-9:  600  QGILPGMVWQDRDVYLQGPIWAKIPHTDGNFHPSPLMGGFGMKHPPPQILIKNTPVPADPPTAFNKDKLNSFITQYSTGQVSVEIEWELQKENSKRWNPE  699

AAV-DJ:      IQYTSNYYKSTSVDFAVNTEGVYSEPRPIGTRYLTRNL*
AAV-2:  698  IQYTSNYNKSVNRGLTVDTNGVYSEPRPIGTRYLTRNL* 735
AAV-8:  701  IQYTSNYYKSTSVDFAVNTEGVYSEPRPIGTRYLTRNL* 738
AAV-9:  700  IQYTSNYYKSNNVEFAVNTEGVYSEPRPIGTRYLTRNL* 735
```

FIG. 1B

AAV CAPSID LIBRARY AND AAV CAPSID PROTEINS

CROSS-REFERENCE TO RELATED APPLICATIONS

This application is a divisional application of currently pending U.S. application Ser. No. 12/538,791, which is a continuation of U.S. application Ser. No. 11/731,314 filed on Mar. 30, 2007 now issued as U.S. Pat. No. 7,588,772, which claims priority to U.S. Provisional Application Ser. No. 60/787,371, filed on Mar. 30, 2006. Each of the aforementioned applications is incorporated herein by reference in its entirety.

STATEMENT REGARDING GOVERNMENT INTEREST

This invention was made with Government support under contracts HL064274 & HL066948 awarded by the National Institutes of Health. The Government has certain rights in this invention.

REFERENCE TO SEQUENCE LISTING, TABLE OR COMPUTER PROGRAM

A "Sequence Listing" is submitted with this application in the form of a text file, created 10 Aug. 2009, and named "586008243US01SEQLIST.txt" (27,932 bytes), the contents of which are incorporated herein by reference in their entirety.

TECHNICAL FIELD

The subject matter described herein relates to libraries of recombinant adeno-associated viral (AAV) plasmids or viruses with varying capsid nucleotide sequences and to methods of generating the libraries. The subject matter also relates to nucleotide sequences isolated from the libraries and to the AAV capsid proteins encoded by these sequences. The subject matter also relates to plasmids and viruses comprising the identified sequences, which preferably provide a high transduction efficiency and a low level of neutralization by the human immune system.

BACKGROUND

Multiple recombinant gene transfer vectors based on different types of viruses have been developed and tested in clinical trials in recent years. Gene transfer vectors based on adeno-associated virus (AAV), i.e., AAV vectors, have become favored vectors because of characteristics such as an ability to transduce different types of dividing and non-dividing cells of different tissues and the ability to establish stable, long-term transgene expression. While vectors based on other viruses, such as adenoviruses and retroviruses may posses certain desirable characteristics, the use of other vectors has been associated with toxicity or some human diseases. These side effects have not been detected with gene transfer vectors based on AAV (Manno et al., *Nature Medicine,* 12(3):342 (2006)). Additionally, the technology to produce and purify AAV vectors without undue effort has been developed.

At least 11 AAV serotypes have been identified, cloned, sequenced, and converted into vectors, and at least 100 new AAV variants have been isolated from non-primates, primates and humans. However, the majority of preclinical data to date that involves AAV vectors has been generated with vectors that are based on the human AAV-2 serotype, which is considered the AAV prototype.

There are several disadvantages to the currently used AAV-2 vectors. For example, a number of clinically relevant cell types and tissues are not efficiently transduced with these vectors. Also, a large percentage of the human population is immune to AAV-2 due to prior exposure to wildtype AAV-2 virus. It has been estimated that up to 96% of all humans are seropositive for AAV-2, and up to 67% of the seropositive individuals carry neutralizing anti-AAV-2 antibodies which could eliminate or greatly reduce transduction by AAV-2 vectors. Moreover, AAV-2 has been reported to cause a cell mediated immune response in patients when given systemically (Manno et al., *Nature Medicine,* 12(3):342 (2006)).

Methods of overcoming the limitations of AAV-2 vectors have been proposed. For example, randomly mutagenizing the nucleotide sequence encoding the AAV-2 capsid by error-prone PCR has been proposed as a method of generating AAV-2 mutants that are able to escape the neutralizing antibodies that affect wildtype AAV-2. However, it is expected that it will be difficult to generate significantly improved AAV-2 variants with single random point mutations, as the naturally occurring serotypes have only about 85% homology at the most in the capsid nucleotide sequence.

Methods of using a mixture of AAV serotype constructs for AAV vectors have also been developed. The resulting chimeric vectors possess capsid proteins from different serotypes, and ideally, thus have properties of the different serotypes used. However, the ratio of the different capsid proteins is different from vector to vector and cannot be consistently controlled or reproduced (due to lack of genetic templates), which is unacceptable for clinical use and not satisfactory for experimental use.

A third approach at modifying the AAV-2 capsid are peptide insertion libraries, in which randomized oligonucleotides encoding up to 7 amino acids are incorporated into a defined location within the AAV-2 capsid. The display of these peptides on the AAV-2 capsid surface can then be exploited to re-target the particles to cells or tissues that are otherwise refractory to infection with the wildtype AAV-2 virus. However, because knowledge of the atomic capsid structure is a prerequisite for this type of AAV modification, this method is currently restricted to AAV serotype 2. Moreover, peptide insertion libraries typically cannot address the issues of AAV particle immunogenicity or transduction efficiency.

Thus, there remains a need for new AAV vectors and a method of generating new AAV vectors. In particular, there is a need for AAV based vectors that can be used efficiently with a variety of cell types and tissues and that do not react with a pre-existing anti-AAV human immunity that could neutralize or inactivate the vectors. There also remains a need for vectors that transduce different cell types in vivo and in vitro and that offer a more restricted biodistribution or a more promiscuous biodistribution, depending on what may be required. In particular, there remains a need for vectors capable of transducing a variety of cells types, such as hematopoietic stem cells or embryonic stem cells.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, recombinant capsid proteins and methods for generating recombinant capsid proteins are provided. The capsid proteins include regions or domains that are derived from different serotypes of AAV. The AAV serotypes may be human or non-human. Recombinant AAV comprising the capsid proteins and plasmids encoding the capsid proteins are also provided.

In one aspect, a capsid protein comprises an individual amino acid or an amino acid sequence from a first AAV serotype, and from at least a second AAV serotype.

In one embodiment, the capsid protein additionally comprises a sequence of amino acid residues from a contiguous sequence of amino acids from a third AAV serotype.

In another embodiment, the sequences of amino acids in the first sequence, in the second sequence, and in the third or further sequence, are each a contiguous sequence of amino acids from the first AAV serotype, the second AAV serotype, the third and/or further AAV serotypes. In another embodiment, the contiguous sequence of amino acids forms a conserved set of amino acid residues, the conserved set having at least about 70% sequence identity, more preferably at least about 80%, still more preferably at least about 85%, and still more preferably at least about 90% or 95% sequence identity with the AAV serotype from a contiguous sequence in its respective AAV serotype.

In one embodiment, the first AAV serotype is AAV-2 and the second AAV serotype is AAV-8 or AAV-9.

In another aspect, a capsid protein comprises an amino acid sequence comprising a first sequence of amino acid residues of a first AAV serotype, a second sequence of amino acid residues of a second AAV serotype, and a third sequence of amino acid residues of a third AAV serotype.

In one embodiment, the first AAV serotype is AAV-2, the second AAV serotype is AAV-8, and the third AAV serotype is AAV-9.

In a preferred embodiment, a capsid protein comprises an amino acid sequence having at least about 80% sequence identity to the amino acid sequence of SEQ ID NO: 1. In another embodiment, the capsid protein is encoded by a nucleotide sequence having at least about 80% sequence identity to the nucleotide sequence of SEQ ID NO: 2.

A viral particle comprising a capsid protein sequence as described above, is contemplated in another embodiment.

In another aspect, a plasmid comprising a sequence selected from the group consisting of (i) sequences having at least 80% sequence identity to SEQ ID NO:2 and (ii) SEQ ID NO: 2 is provided.

In yet another aspect, a recombinant AAV vector is provided, the vector comprising a capsid protein having an amino acid sequence selected from the group of sequences consisting of (i) sequences having at least 80% sequence identity to SEQ ID NO:1 and (ii) SEQ ID NO: 1.

In still another aspect, a method of expressing a gene of interest in a mammal is provided. The method comprises introducing a recombinant AAV vector into a mammal, the recombinant AAV vector encoding for a gene of interest which is encapsidated into a capsid protein having an amino acid sequence selected from the group of sequences consisting of (i) sequences having at least 80% sequence identity to SEQ ID NO:1 and (ii) SEQ ID NO:1.

In still another aspect, a method of generating a library of recombinant AAV plasmids is disclosed, the method comprising: isolating AAV capsid nucleotide sequences from two or more serotypes of AAV; digesting the AAV capsid nucleotide sequences into fragments; reassembling the fragments using PCR to form PCR products; and cloning the re-assembled PCR products into plasmids to generate a library of recombinant AAV plasmids.

In one embodiment, the method includes isolating AAV capsid nucleotide sequences from human AAV serotypes and non-human AAV serotypes. Exemplary serotypes include AAV-2, AAV-8, and AAV-9.

In another embodiment, the method comprises transfecting cells with the plasmids to produce a viral library, preferably an AAV viral library.

In one embodiment, the transfection includes transfecting into 293 kidney cells with a helper Adenovirus.

In another embodiment, the method additionally includes, after the transfecting, passaging the viral library in a selected cell type in the presence of a stringent condition, and selecting AAV capsids that survive the passaging. Passaging can be for several or multiple passages, for example from between 2-5 or 2-10 passages.

In one embodiment, a stringent condition comprises the presence of human immune globulin.

In another aspect, a library prepared according to the methods described above is disclosed. In one embodiment the library is comprised of plasmids of shuffled full-length capsid genes and in another embodiment the library is comprised of viral particles obtained by transfecting all or a portion of the plasmid library into a selected cell, optionally in combination with an adenoviral helper plasmid.

In addition to the exemplary aspects and embodiments described above, further aspects and embodiments will become apparent by reference to the drawings and by study of the following descriptions.

BRIEF DESCRIPTION OF THE DRAWINGS

FIG. 1A and FIG. 1B show an alignment of the amino acid sequences of AAV-DJ (SEQ ID NO: 1) and of the capsid proteins of AAV-2 (SEQ ID NO: 3), AAV-8 (SEQ ID NO: 4), and AAV-9 (SEQ ID NO: 5);

BRIEF DESCRIPTION OF THE SEQUENCES

Figure 2A:
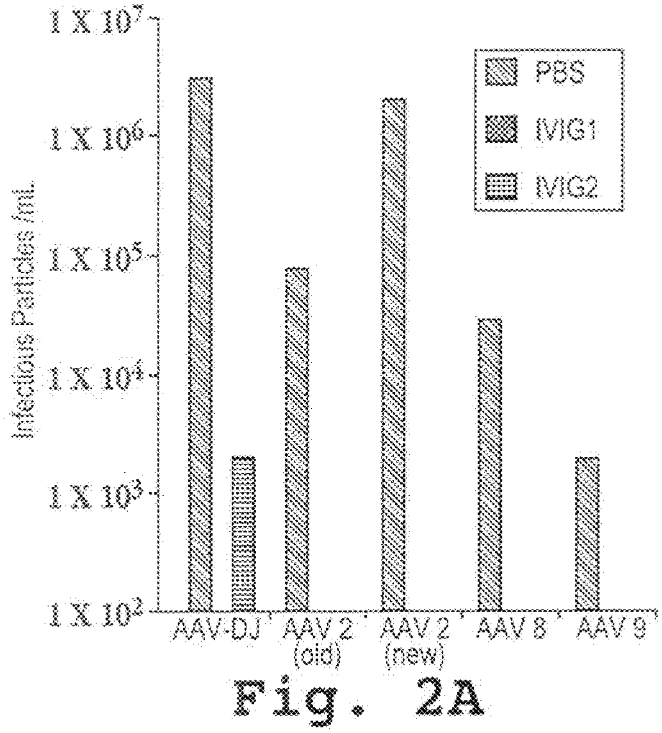
FIGS. 2A-2C are graphs showing the infectious particles per mL of AAV-DJ viral particles, AAV-2, AAV-8, and AAV-9 after neutralizing assays using human immune globulin (IVIG) in 293 cells (FIGS. 2A, 2C), Huh-7 cells (FIG. 2B) at antiserum to virus dose ratios of 1:1 (FIGS. 2A-2B) or 1:2 (high), 1:10 (med), and 1:25 (low) (FIG. 2C)

SEQ ID NO:1 is an amino acid sequence of a novel recombinant VP1 capsid protein, referred to herein as AAV-DJ.

SEQ ID NO:2 is a nucleotide sequence encoding the protein AAV-DJ.

SEQ ID NO:3 is the amino acid sequence of the capsid protein of AAV-2.

SEQ ID NO:4 is the amino acid sequence of the capsid protein of AAV-8.

SEQ ID NO:5 is the amino acid sequence of the capsid protein of AAV-9.

SEQ ID NOS:6-15 are artificial primers.

DETAILED DESCRIPTION

I. Definitions

The practice of the subject matter described herein will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995) and ANIMAL CELL CULTURE (R. I. Freshney. Ed., 1987).

As used in this specification and the appended claims, the singular forms "a," "an" and "the" include plural references unless the content clearly dictates otherwise.

A polynucleotide is typically composed of a specific sequence of four nucleotide bases: adenine (A); cytosine (C); guanine (G): and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences in association therewith.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul. *Proc. Natl. Acad. Sci. USA* 87:2264-2268 (1990) and as discussed in Altschul, et al., *J. Mol. Biol.* 215:403-410 (1990); Karlin And Altschul, *Proc. Natl. Acad. Sci. USA* 90:5873-5877 (1993); and Altschul et al., *Nucleic Acids Res.* 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Default parameters are provided to optimize searches with short query sequences in, for example, blastp with the program. The program also allows use of an SEG filter to mask-off segments of the query sequences as determined by the SEG program of Wootton and Federhen, *Computers and Chemistry* 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80-85%, preferably 85-90%, more preferably 90-95%, and most preferably 98-100% sequence identity to the reference sequence over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

II. Chimeric AAV Capsid

In one aspect, capsid proteins with regions or domains or individual amino acids that are derived from two or more different serotypes of AAV are provided. In one embodiment, described below, a capsid protein comprised of a first region that is derived from a first AAV serotype, a second region that is derived from a to second AAV serotype, and a third region that is derived from a third AAV serotype is provided. The AAV serotypes may be human AAV serotypes or non-human AAV serotypes, such as bovine, avian, and caprine AAV serotypes. In particular, non-primate mammalian AAV serotypes, such as AAV sequences from rodents (e.g., mice, rats, rabbits, and hamsters) and carnivores (e.g., dogs, cats, and raccoons), may be used. By including individual amino acids or regions from multiple AAV serotypes in one capsid protein, capsid proteins that have multiple desired properties that are separately derived from the multiple AAV serotypes may be obtained.

In one embodiment, a capsid protein, referred to herein as "AAV-DJ", that has an amino acid sequence comprising a first region that is derived from a first AAV serotype (AAV-2), a second region that is derived from a second AAV serotype (AAV-8), and a third region that is derived from a third AAV serotype (AAV-9), is provided. The AAV-DJ capsid protein was identified from a library of capsid proteins, the library generated using a method described below (Example 1). It will be appreciated that the AAV-DJ protein is merely exemplary of the beneficial capsid proteins that can be obtained from a library generated according to the teachings herein, where the beneficial capsid proteins preferably have multiple desired properties that are derived from multiple AAV serotypes.

The amino acid sequence of AAV-DJ is shown in SEQ ID NO: 1, and the nucleotide sequence encoding AAV-DJ is shown in SEQ ID NO: 2. FIGS. 1A and 1B show an alignment of the amino acid sequences of AAV-DJ and of the capsid proteins of AAV-2 (SEQ ID NO:3), AAV-5 (SEQ ID NO:4), and AAV-9 (SEQ ID NO:5). The five boxes numbered 1-5 in FIGS. 1A and 1B represent the five known loops on the exterior of the AAV-2 capsid which are likely to be involved in capsid binding to cellular receptors and recognized by neutralizing antibodies. The alignment in FIGS. 1A and 1B show that the N-terminus of AAV-DJ is identical to the N-terminus of the AAV-2 capsid protein and that the C-terminus of AAV-DJ is identical to the C-terminus of the AAV-8 capsid protein. The loop 1 region of AAV-DJ is identical to the loop 1 region of AAV-9. The loop 2, 3, and 5 regions of AAV-DJ are identical to the corresponding regions of AAV-8. The loop 4 region of AAV-DJ is a hybrid of the loop 4 regions of AAV-2 and AAV-8, with parts of the AAV-DJ loop 4 region being identical to parts of the loop 4 region of AAV-2, parts of the AAV-DJ loop 4 region being identical to parts of the loop 4 region of AAV-8, and parts of the loop 4 region of AAV-DJ being identical to both parts of the loop 4 region of AAV-2 and of AAV-8.

AAV-DJ has four mismatches to the two T cell epitopes in AAV-2 which have recently been identified as being involved in an anti-AAV cytotoxic T lymphocyte (CTL) response in humans. Thus, recombinant AAV vectors that include the AAV-DJ capsid protein or a derivative thereof are likely less immunogenic in humans than AAV-2 vectors that include the AAV-2 capsid.

Studies were conducted to confirm that infectious viral particles can be formed with AAV-DJ as the capsid. In a first study, the AAV-DJ nucleotide sequence was inserted into an AAV helper plasmid that also expresses the AAV-2 rep gene (Example 2). 293 kidney cells were then co-transfected with the AAV helper plasmid and an adenoviral helper plasmid, as well as a gfp-expressing vector plasmid. For comparison, two different versions of an AAV-2 helper were used (designated AAV-2 "old" and AAV-2 "new") which differ in the expression levels of viral proteins. Three days after the co-transfection, Western blotting (with 303.9 (Rep) and B1 (capsid protein)) of the 293 cell extracts revealed the presence of presence of Rep and capsid proteins at levels comparable to those found in cells co-transfected with plasmids expressing the AAV-2, AAV-8, or AAV-9 capsid proteins (blot not shown).

In another study, particle infectivity and ability to avoid neutralization by human immune globulin (IVIG) of AAV-DJ clone was compared to wildtypes AAV-2, AAV-8, and AAV-9. Two different versions of an AAV-2 helper were used (designated AAV-2 old and AAV-2 new) which differ in the expression levels of viral proteins. Recombinant AAVs with either the AAV-DJ, AAV-2, AAV-8, or AAV-9 capsids were produced by triple transfecting cells with a plasmid encoding gfp flanked by AAV inverted terminal repeats (ITRs), a plasmid encoding adenoviral helper genes, and a plasmid encoding the AAV-2 Rep gene and either the AAV-DJ, AAV-2, AAV-8, or AAV-9 capsid protein, and then freeze-thaw lysing the cells. Each virus-containing lysate was then neutralized using a high dose (1:1 volume) of two different batches of human immune globulin (IVIG1 and IVIG2) (FIG. 2A (293 cells); FIG. 2B (Huh-7 cells)), or three decreasingly lower doses (1:2 (high), 1:10 (med), and 1:25 (low) antiserum/virus) of the two different batches of human immune globulin (IVIG1 and IVIG2), or a monoclonal A20 antibody (FIG. 2C, 293 cells), or a polyclonal anti-AAV-8 serum ("A8"). A20 is a monoclonal antibody that was raised against assembled AAV-2 capsids and anti-AAV-8 is a polyclonal rabbit serum raised against assembled AAV-8 capsids. Lysates treated with PBS were used as a control. The virus-containing lysates were neutralized by incubating the lysates with the human immune globulin or antibody for a period of time (one hour at room temperature (20-25° C.)) and then infecting cells in the presence of helper adenovirus. The remaining activity of the viruses after the neutralization period was determined by titrating gfp expression units on the cells.

Figure 2B:
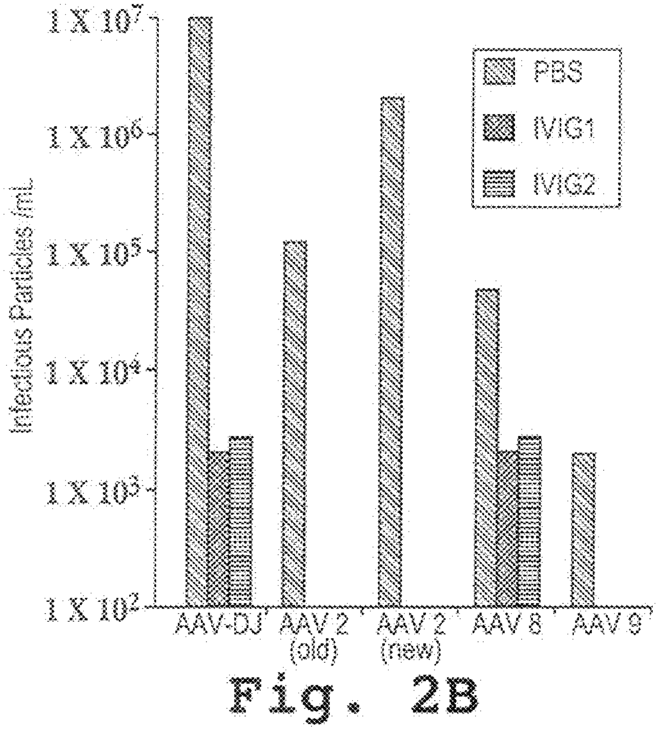
Figure 2C:
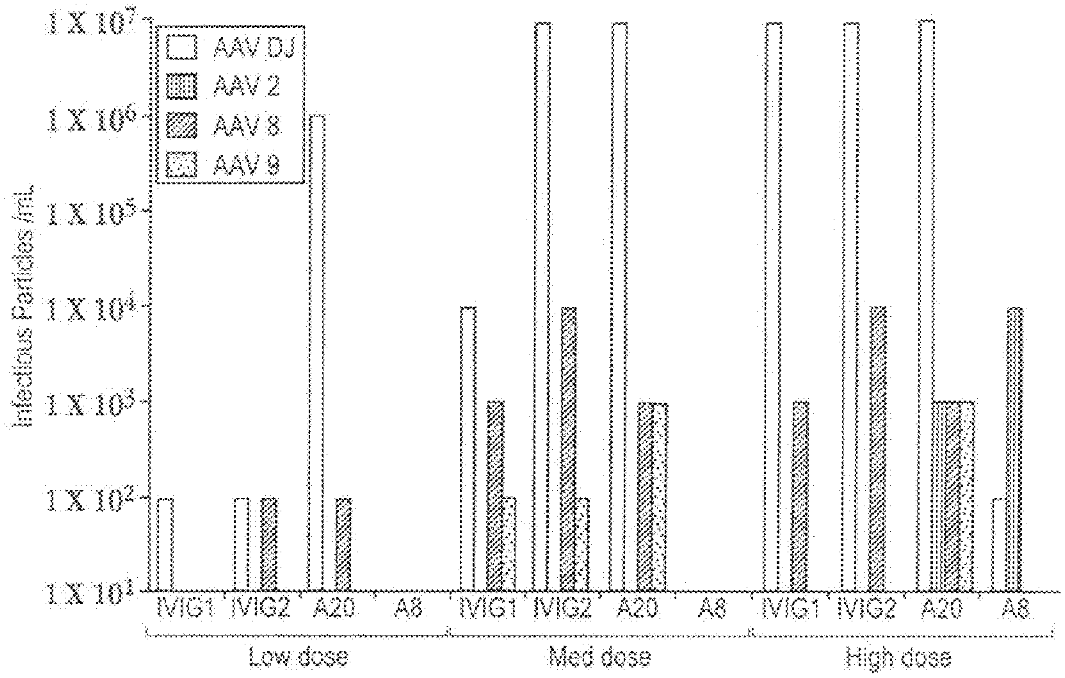

The results for the 293 cells are shown in FIG. 2A and for the Huh-7 cells in FIG. 2B. In the absence of IVIG1, IVIG2, and A20, the AAV-DJ virus was at least as infectious on 293 cells as AAV-2 and several fold more infectious than AAV-2 on Huh-7 cells. The data also shows that the AAV-DJ virus and AAV-8 were able to partially escape neutralization by IVIG, while AAV-2 was not. AAV-9 had intermediate IVIG results relative to AAV-DJ/AAV-8 and AAV-2, and was neutralized at high IVIG doses. AAV-2 was neutralized by the A20 antibody, but the A20 antibody did not significantly affect AAV-DJ, AAV-8, or AAV-9. The polyclonal anti-AAV-8 antiserum neutralized all four capsids at high or medium doses, whereas AAV-2 and AAV-DJ partially escaped neutralization at the low dose.

In summary, it was found that the AAV-DJ virus was more infectious to Huh-7 cells than the previously known most efficient AAV on Huh-7 cells (AAV-2) even in the presence of high concentrations of human immune globulin. Also, the AAV-DJ virus was found to have improved resistance to neutralization by human immune globulin relative to AAV-2. Such resistance is reasonable, given that the AAV-DJ capsid was selected from a library partially based on its ability to produce virus that resist neutralization by human immune globulin. However, the improved resistance of the AAV-DJ virus to the A20 antibody was surprising and unexpected, because (i) it was not part of the selection scheme described below that was used to isolate AAV-DJ; and (ii) AAV-DJ shares substantial identity to AAV-2, which is neutralized by the A20 antibody.

Figure 3:
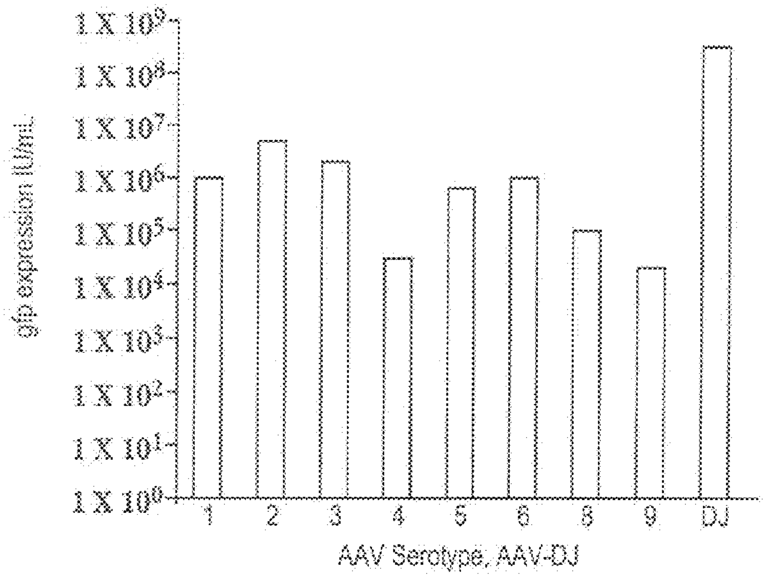
FIG. 3 is a bar graph showing green fluorescent protein (gfp) expression, in IU/mL, in human melanoma cells in vitro following transduction with recombinant AAV-DJ particles or with wildtype MV-1, AAV-2, AAV, 3, AAV-4, AAV-5, AAV-6, AAV-8, or AAV-9 particles that express gfp.

In yet another study using human melanoma cell, in vitro infectivity of gfp-expressing vectors from the AAV-DJ capsid gene was compared to the in vitro infectivity of eight commonly used wildtype AAVs, AAV-1, AAV-2, AAV-3, AAV-4, AAV-5, AAV-6, AAV-8, or AAV-9. The melanoma cells were infected with $2\times10^9$ recombinant AAV particles of each serotype and gfp expression was visualized three days later. The quantative results, expressed as gfp expression in IU/mL, from virus titration on the melanoma cells (in 96-well plates) are shown in FIG. 3. The AAV-DJ vector was superior to the wildtype vectors, and, notably, substantially better than AAV-2.

A number of cell lines were infected with ten-fold serial dilutions of each serotype, or AAV-DJ or the DJ heparin mutant DJ/8, discussed below, expressing a gfp reporter gene. Vector preparations were normalized to contain $2\times10^9$ total (vector DNA-containing) particles per mL prior to infection. Three days later, gfp-expressing cells were counted and infectious titers determined, taking into account the dilution factor. As seen in Table 1, AAV-DJ vectors showed the highest infectivity on all tested cell lines, and ratios of total to infectious particles were frequently far below 500, highlighting the extreme efficiency of AAV-DJ in vitro, and suggesting its particular usefulness for ex vivo gene transfer applications.

months after injection. The FIX protein plasma levels were quantified by ELISA, and the results are shown in FIGS. 4A-4C.

Figure 4A:
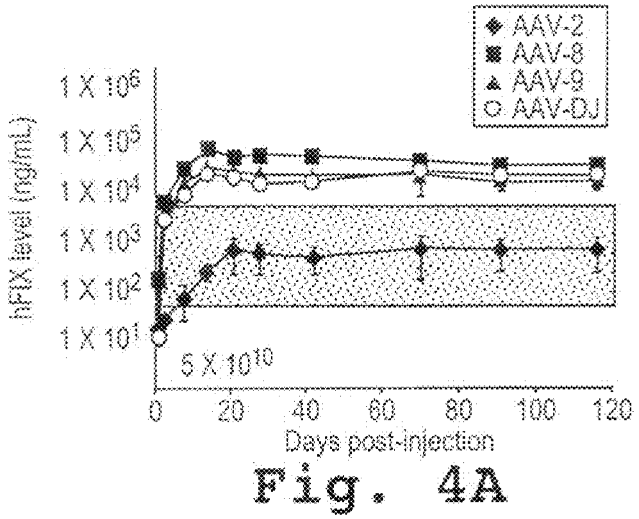
FIGS. 4A-4C are graphs showing the amount of factor IX protein (ng/mL) in mice, as a function of days post-injection of AAV-DJ (circles), AAV-2 (diamonds), AAV-8 (squares), or AAV-9 (triangles) expressing human factor IX (FIX) gene at doses of $5\times10^{10}$ (FIG. 4A), $2\times10^{11}$ (FIG. 4B), and $1\times10^{12}$ (FIG. 4C)
Figure 4B:
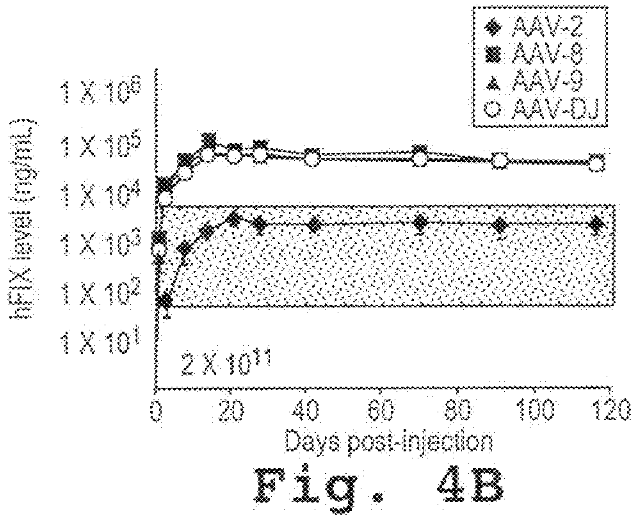
Figure 4C:
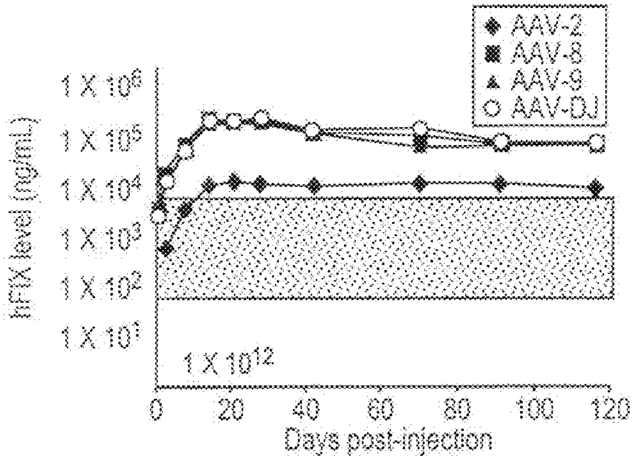

In FIGS. 4A-4C, the shading represents 1-100% normal hFIX levels in humans (0.05 to 5 μg/mL). FIX levels over 1% are considered therapeutic in hemophilics. As seen, the AAV-8, -9 or -DJ vectors exceeded the 100% level already at the lowest dose. A dose-dependent expression from the AAV-DJ capsid at levels equivalent to AAV-8 and -9, the best two naturally identified AAVs reported in liver thus far, was observed. All three viruses readily outperformed the AAV-2 prototype at any dose and expressed over 100% of normal hFIX levels from intravenous injection of $5\times10^{10}$ particles, whereas AAV-2 expression was over 100% of normal hFIX levels only at a dose of $1\times10^{12}$.

Figure 5:
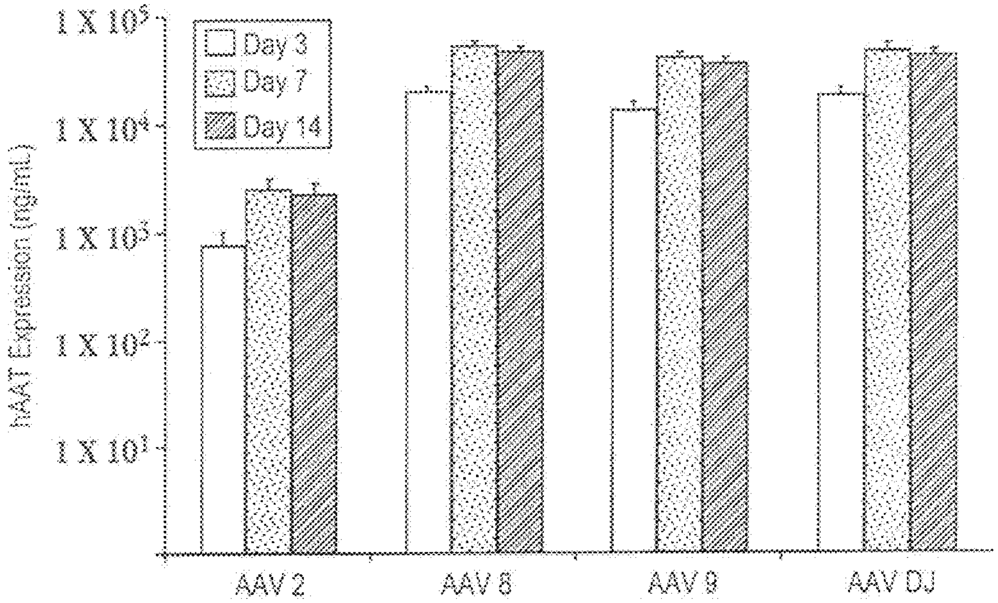
FIG. 5 is a bar graph showing the expression of human alpha-1-antitrypsin (hAAT), in ng/mL, in mice injected with identical doses ($2\times10^{11}$) of recombinant AAV-2, AAV-8, AAV-9, or AAV-DJ vectors expressing hAAT, the expression measured 3 (open), 7 (dotted) or 14 (cross-hatched) days after injection.

In another study, recombinant human alpha-1-antitrypsin (hAAT)-expressing AAVs were prepared, from the AAV-DJ, AAV-2, AAV-8, or AAV-9 capsids. The hAAT gene was under an RSV promoter. Mice (C57/BL6) were injected via tail vein infusions of $2\times10^{11}$ particles and plasma levels of hAAT were determined via specific ELISA 3, 7, and 14 days after injection. Results are shown in FIG. 5. AAV-8, AAV-9, and AAV-DJ expressed efficiently and equally outperformed the vector with an AAV-2 capsid.

Figure 6A:
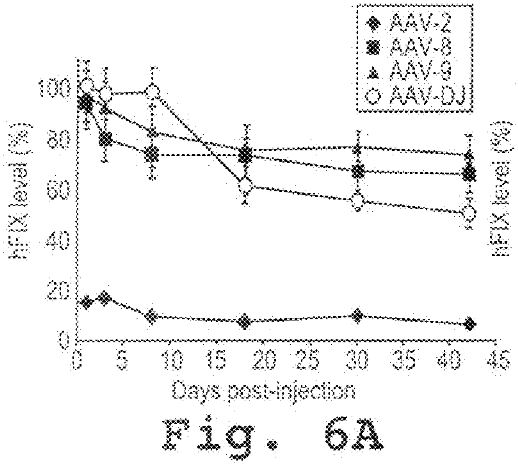
FIGS. 6A-6B are graphs showing plasma hFIX levels in mice immunized with 4 mg (FIG. 6A) or 20 mg (FIG. 6B) IVIG prior to injection of hFIX-expressing AAV-DJ (open circles), AAV-2 (closed diamonds), AAV-8 (closed squares), or AAV-9 (closed triangles) as a function of time post-injection, the hFIX levels shown as a percent of the corresponding level in control mice treated with phosphate-buffered saline rather than IVIG.
Figure 6B:
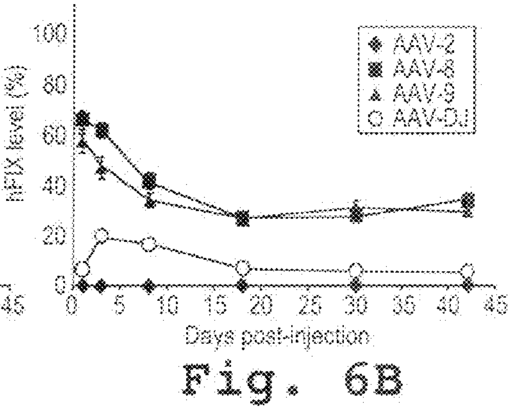

In another in vivo study, liver transduction in the presence of human serum was quantified, to assess the ability of AAV-DJ to evade neutralization in vivo. As described in Example 4, mice were passively immunized with 4 or 20 mg IVIG prior to infusion of hFIX-expressing AAV-2, -8, -9, or -DJ. Plasma hFIX levels for each AAV serotype are shown in FIGS. 6A-6B as percent corresponding virus level in control mice treated with phosphate-buffered saline rather than IVIG as a function of time post infusion. FIG. 6A shows the results for mice immunized with 4 mg IVIG and FIG. 6B shows the results for mice immunized with 20 mg IVIG. AAV-2 expression was

TABLE 1

In vitro infectivity of AAV-DJ and wildtype vectors

| Cell line | Tissue[2] | Ratio of Total to Infectious AAV particles[1] ($\times10^3$) AAV 1 | AAV 2 | AAV 3 | AAV 4 | AAV 5 | AAV 6 | AAV 8 | AAV 9 | AAV DJ | AAV DJ/8 |
|---|---|---|---|---|---|---|---|---|---|---|---|
| Huh-7 | hu liver | 4 | 0.5 | 20 | 2000 | 400 | 5 | 70 | 7000 | 0.1 | 300 |
| 293 | hu kidney | 2 | 0.5 | 20 | 700 | 400 | 10 | 70 | 700 | 0.1 | 200 |
| HeLa | hu cervix | 70 | 2 | 100 | 2000 | 30 | 200 | 1000 | 2000 | 0.3 | 1000 |
| HepG2 | hu liver | 2000 | 50 | 300 | 20000 | 3000 | 1000 | 20000 | nd | 4 | 10000 |
| Hep1A | mu liver | 10 | 2 | 1000 | 200 | 2000 | 200 | 1000 | 20000 | 0.5 | 2000 |
| 911 | hu retina | 6 | 1 | 9 | 500 | 700 | 6000 | 1000 | nd | 0.2 | 400 |
| CHO | ha ovary | 10 | 10 | 70 | 700 | 3 | 20 | 100 | 1000 | 0.04 | 200 |
| COS | si kidney | 3 | 1 | 3 | 30 | 20 | 7 | 50 | 200 | 0.2 | 300 |
| MeWo | hu skin | 2 | 0.2 | 1 | 70 | 3 | 2 | 20 | 100 | 0.007 | 20 |
| NIH3T3 | mu fibrobl. | 200 | 20 | 700 | 700 | 7000 | 200 | 7000 | nd | 4 | 20000 |
| A549 | hu lung | 70 | 10 | 50 | nd | 2000 | 100 | 2000 | 7000 | 1 | 20000 |
| HT1180 | hu fibrobl. | 50 | 10 | 100 | 7000 | 3000 | 30 | 2000 | 10000 | 3 | 5000 |

[1]Numbers shown are average ratios (rounded) of total to infectious AAV particles from at least three independent titrations. Lower numbers indicate higher infectivity.
[2]hu, human; mu, murine; ha, hamster; si, simian: fibrobl., fibroblasts; nd, not delectable ($>2\times10^7$).

Vectors prepared with the AAV-DJ capsid were also tested in vivo for expression of a gene of interest. In a first study, recombinant human factor IX (FIX)-expressing AAVs with either the AAV-DJ, AAV-2, AAV-8, or AAV-9 capsids were produced by a triple transfection technique described in Example 3. Doses of $5\times10^{10}$, $2\times10^{11}$, and $1\times10^{12}$ (low, medium, and high, respectively) recombinant viral particles were injected peripherally into immunocompetent mice (C57/BL6) and plasma hFIX was monitored for up to four completely abolished, however transduction with AAV-DJ, -8 or -9 was inhibited in a dose-dependent manner, with AAV-DJ showing intermediate resistance at the high, and efficient evasion (similar to AAV-8 and AAV-9) at the low IVIG dose (FIG. 6A). These results were confirmed with a second independent IVIG batch from another vendor (Carimune 12%, Behring AG, data not shown).

Figure 6C:
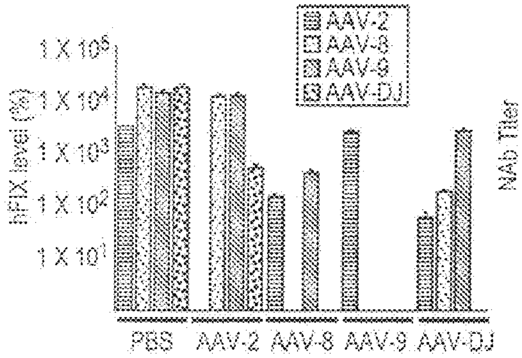
FIG. 6C is a bar graph showing the hFIX plasma concentration, in ng/mL, in mice injected with PBS or hAAT-expressing AAV-2, -8, -9 or -DJ (X axis), and three weeks later re-injected hFIX-expressing viruses, the hFIX plasma concentrations measured six weeks after the second injection.
Figure 6D:
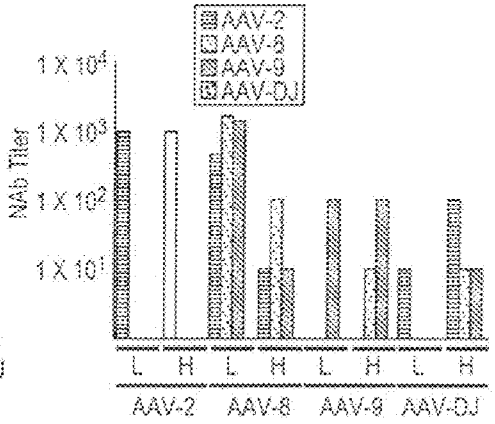
FIG. 6D is a bar graph showing neutralizing antibody titers (NAb) against the wildtype AAVs or AAV-DJ in sera taken from the mice, treated as described in FIG. 6C, at the time of re-injection (H), as well as from a parallel group injected with a lower dose (L) of $2\times10^{10}$ particles.

In another study, also described in Example 4, the feasibility to repeatedly administer the different viruses to mice was assessed, to evaluate capsid cross-neutralization. Results are shown in FIG. 6C. No gene expression upon re-infusion of any of the capsids into animals already treated with the same serotype was observed. However, AAV-8 and -9 also efficiently blocked each other, substantiating previous data (Gao, G. et al., *J. Virol.,* 78:6381-6388 (2004)). This result might argue against the use of vectors based on these wildtypes in re-administration protocols, albeit they could be combined with AAV-2. In contrast, primary infusion of AAV-DJ allowed subsequent expression (up to 18%) from AAV-2, -8 or -9, likely due to the fact that AAV-DJ only shares a limited number of epitopes with each wildtype virus. In the reverse experiment, AAV-DJ vectors were inhibited in animals immunized with AAV-8 or -9, while giving detectable expression in AAV-2-treated mice. This implied a stronger or broader immune response from primary infusion of serotypes 8 or 9. AAV-DJ was more resistant to the corresponding mouse sera in culture, as seen in FIG. 6D. Less cross-reactivity between AAV-8 and -9 was noted.

Figure 7A:
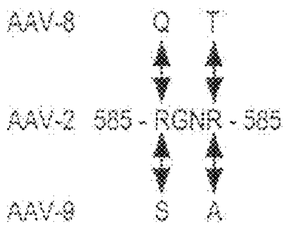
FIG. 7A shows amino acid residues at positions 585-588 in AAV-2 and the modifications at the two arginine (R) residues in AAV-2, AAV-8, AAV-9, or AAV-DJ mutagenized to eliminate or introduce a heparin binding domain.

AAV-DJ, as well as other recombinant protein capsids identified in the library discussed below, retained a heparin binding domain (HBD) from the AAV-2 parent. This domain functions in binding to the primary AAV-2 receptor heparin sulfate proteoglycan (Summerford, C. et al., *J. Virol.,* 72:1438-1445 (1998)). To investigate the role of the AAV-DJ HBD, two crucial arginine residues (Kern, A. et al., *J. Virol.,* 77:11072-11081 (2003)) were mutated to the respective residues in AAV-8 or -9, as shown in FIG. 7A, and are referred to herein as AAV-DJ/8 and AAV-DJ/9. Table 1 above includes data on the mutant AAV-DJ/8, and shows that gfp expression was reduced by several orders of magnitude, and was as low as that observed with serotypes AAV-8 or AAV-9.

Figure 7B:
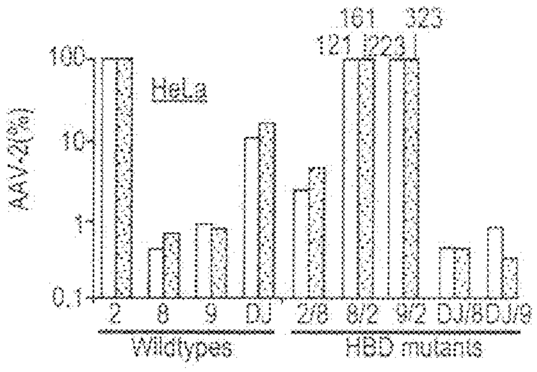
FIG. 7B is a bar graphs showing the titration of infectious particles on kidney cells, in IU/mL for AAV-2, AAV-8, AAV-9, AAV-DJ, and for the mutants (FIG. 7A) AAV-2/8, AAV-8/2, AAV-9/2. AAV-DJ/8, and AAV-DJ/9.
Figure 7C:
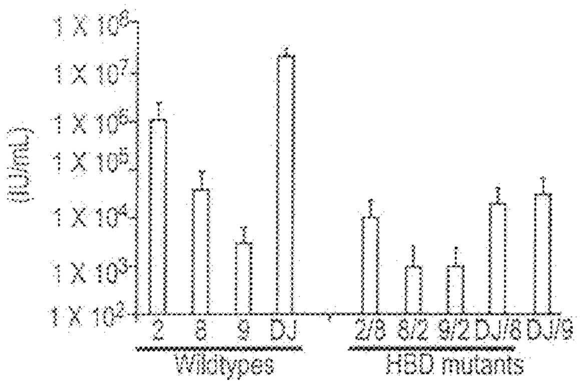
FIGS. 7C-7D are bar graphs of cells binding assays in HeLa (FIG. 7C) and Huh-7 (FIG. 7D) cells, showing the binding, expressed as a percentage of AAV-2, of AAV-2, AAV-8, AAV-9, AAV-DJ, and for the mutants (FIG. 7A) AAV-2/8, AAV-8/2, AAV-9/2, AAV-DJ/8, and AAV-DJ/9.
Figure 7D:
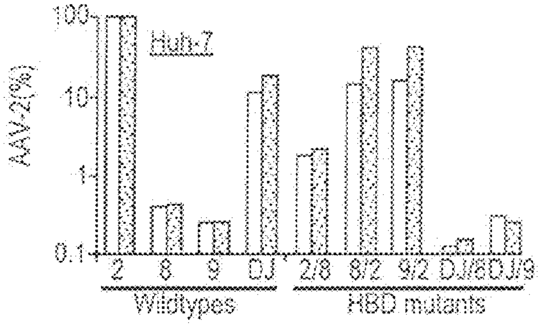

The infectivity drop (Table 1) was shown to correlate with a reduced binding to cells. As seen in FIG. 7B, a titration of infectious particles on 293 kidney cells illustrated the role of the HBD for infection in culture, as seen by the reduction in infectivity in the HBD mutants AAV-DJ/8 and AAV-DJ/9. Additional mutants were prepared and tested, and are identified herein as AAV-2/8 (HBD negative), AAV-8/2 (HBD positive), and AAV-9/2 (HBD positive). Cell binding assays, shown in FIGS. 7C-7D, confirmed the role of the HBD for attachment to cultured cells, where the drop in binding with the mutants correlated with the transduction data in FIG. 7B. The HBD-positive AAV-8 and AAV-9 mutants bound several fold more efficiently than AAV-2 on HeLa cells (FIG. 7C), but transduced less efficiently. Thus, cell attachment alone cannot explain the unusual infectivity of AAV-DJ. Instead, a synergistic effect from sharing beneficial properties from all AAV-DJ parents is contemplated, resulting in enhancement of multiple steps in AAV-DJ transduction.

The HBD also was shown to influence biodistribution, as shown in Table 2. AAV-8 and -9 (HBD-negative) demonstrated an unrestricted tropism, readily transducing all tested tissues at $1\times10^{12}$ particles per mouse. In striking contrast, AAV-2 and likewise AAV-DJ (both HBD-positive) were restricted to liver and, to a lesser extent, heart, kidney and spleen, and near or below detection limit in all other tissues. Quantification of double-stranded vector DNA (using liver as an internal standard in each group) showed that AAV-DJ transduced lung, brain, pancreas and gut about 2- to 4-fold less efficiently than wildtypes 8 or 9. The effect of the HBD on viral tropism was best exemplified by comparing AAV-DJ to the DJ/8 mutant: HBD deletion alleviated the liver restriction and expanded transduction to all nonhepatic tissues, identical to AAV-8 and -9, and including the brain. These findings corroborate and explain a series of reports on wide tissue dissemination of vectors based on HBD-negative natural serotypes (AAV-1 and -4 to –9) in mice, dogs and monkeys, in contrast to the HBD-positive AAV-2. Notably, AAV-DJ also transduced nonhepatic tissues at the maximum dose of $7\times10^{12}$ particles, but still to a lesser extent than the HBD-negative viruses, in particular AAV-9. Even at this dose, brain and also lung transduction remained marginal.

TABLE 2

Relative transduction of non-hepatic tissues with AAV vectors

| | | Lung | Heart | Kidney | Spleen | Brain | Pancreas | Gut | Muscle |
|---|---|---|---|---|---|---|---|---|---|
| AAV-2 | 1e12 | nd | 0.7 ± 0.1 | 0.8 ± 0.1 | 0.2 ± 0.0 | nd | nd | nd | nd |
| | 7e12 | nd | 1.5 ± .03 | 2.0 ± 0.3 | 1.0 ± 0.2 | nd | nd | nd | nd |
| AAV-8 | 1e12 | 0.5 ± 0.0 | 1.2 ± 0.2 | 0.9 ± 0.2 | 0.3 ± 0.0 | 0.2 ± 0.0 | 0.2 ± 0.0 | 0.3 ± 0.0 | 0.7 ± 0.1 |
| | 7e12 | 2.5 ± 0.3 | 2.5 ± 0.2 | 2.6 ± 0.3 | 1.5 ± 0.2 | 1.5 ± 0.2 | 1.2 ± 0.2 | 1.2 ± 0.2 | 1.9 ± 0.2 |
| AAV-9 | 1e12 | 0.7 ± 0.1 | 1.3 ± 0.2 | 1.1 ± 0.2 | 0.4 ± 0.0 | 0.2 ± 0.0 | 0.2 ± 0.0 | 0.3 ± 0.0 | 0.8 ± 0.1 |
| | 7e12 | 2.6 ± 0.3 | 3.6 ± 0.4 | 3.8 ± 0.4 | 1.5 ± 0.2 | 1.8 ± 0.2 | 1.3 ± 0.2 | 1.9 ± 0.2 | 3.0 ± 0.3 |
| AAV-DJ | 1e12 | 0.2 ± 0.0 | 1.3 ± 0.2 | 0.8 ± 0.2 | 0.5 ± 0.1 | nd | 0.1 ± 0.0 | 0.1 ± 0.0 | 0.2 ± 0.0 |
| | 7e12 | 0.6 ± 0.1 | 2.3 ± 0.2 | 2.1 ± 0.2 | 1.5 ± 0.2 | 0.4 ± 0.0 | 0.5 ± 0.0 | 0.5 ± 0.0 | 0.8 ± 0.1 |
| AAV-DJ/8 | 1e12 | 0.6 ± 0.0 | 1.3 ± 0.2 | 0.8 ± 0.2 | 0.2 ± 0.0 | 0.2 ± 0.0 | 0.1 ± 0.0 | 0.2 ± 0.0 | 0.7 ± 0.1 |
| | 7e12 | 2.6 ± 0.3 | 2.5 ± 0.3 | 2.3 ± 0.3 | 1.6 ± 0.3 | 1.8 ± 0.2 | 1.2 ± 0.2 | 1.3 ± 0.2 | 2.0 ± 0.2 |

Vector copy numbers (per diploid genomic equivalent) were determined via Phosphoimager scan analyses of Southern Blots. At least three independent mice were analysed per dose. Copy numbers are shown in percent (rounded to one decimal, plus standard deviations) relative to those in liver within each group, allowing comparison between vectors and doses. For AAV-2, most signals were below the detection limit of the Southern Blot analyses (~0.03 copies of double-stranded AAV DNA per cell), preventing calculation of relative transduction in these cases (nd, not determined). Grey shadows highlight doses/tissues where relative AAV-DJ transduction differed by at least 2-fold from serotypes 8 and 9, as well as the AAV-DJ HBD mutant.

While the embodiments described above are primarily with respect to an AAV-DJ capsid having the amino acid sequence of SEQ ID NO: 1 and the nucleotide sequence of SEQ ID NO: 2, it is recognized that capsids having amino acid and/or nucleotide sequences that are similar in sequence to SEQ ID NO: 1 and SEQ ID NO: 2 and having the same function may be used and are contemplated. In one embodiment, a recombinant capsid protein having at least about 60% identity, further at least about 70% identity, preferably at least about 80% identity, more preferably at least about 90% identity, and further preferably at least about 95% identity, to the amino acid sequences identified as SEQ ID NO:1 is contemplated.

It will be appreciated that conservative amino acid substitutions may be to the protein of SEQ ID NO:1, to achieve proteins having, for example, 60%, 70%, 80%, 90%, or 95% sequence identity to SEQ ID NO:1, and preferably with retention of activity of the native sequence. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, amino acids having acidic side chains, such as aspartic acid and glutamic acid, are considered interchangeable herein with amino acids having amide side chains, such as asparagine and glutamine.

In one embodiment, the recombinant AAV capsid protein is comprised of a first sequence of amino acid residues from a first AAV serotype, and at least a second sequence of amino acid residues from a second AAV serotype. The first sequence is, in the embodiment, a conserved set of amino acids from a contiguous sequence of amino acids from the first AAV serotype. The second sequence is a conserved set of amino acids from a contiguous sequence of amino acids from the second AAV serotype. A “conserved set” of amino acids refers to a contiguous sequence of amino acids that is identical or closely homologous to a sequence of amino acids in the AAV serotype. In one embodiment, close homology intends at least about 80% sequence identity. A contiguous sequence of amino acids in such a conserved set may be anywhere from 2 to 500, 2 to 400, 2 to 300, 2 to 200, 2 to 100, or 2 to 50 amino acid residues in length.

It will also be appreciated that the recombinant vectors described herein are contemplated for use in methods of expressing a gene of interest in a variety of cells and in a mammal. Transduction into cells lines in addition to the cell lines described herein, for example in Table 1, are exemplary, and other cells lines, particularly stem cells, are contemplated. In terms of in vivo use, the method preferably comprises introducing a recombinant AAV into the mammal, the recombinant AAV encoding the gene of interest and comprising a capsid protein having an amino acid sequence selected from the group of sequences consisting of (i) sequences having 80% sequence identity to SEQ ID NO:1 and (ii) SEQ ID NO: 1. The vector expressing a gene of interest is introduced to the mammal, typically by injection, intravenously, subcutaneously, parenterally, or the like. The gene of interest can be any gene, and many suitable genes for expression for therapeutic or non-therapeutic purposes are readily identified by a skilled artisan. The nucleotide sequence of the gene of interest is typically “operably linked” to one or more other nucleotide sequences, including but not limited to the gene for a selected capsid protein, a promoter, and enhancer, and the like.

A gene is “operably linked” to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous. Additionally, as defined herein, a nucleotide sequence is intended to refer to a natural or synthetic linear and sequential array of nucleotides and/or nucleosides, and derivatives thereof. The terms “encoding” and “coding” refer to the process by which a nucleotide sequence, through the mechanisms of transcription and translation, provides the information to a cell from which a series of amino acids can be assembled into a specific amino acid sequence to produce a polypeptide.

III. Generation of a Library of Novel AAV Capsids

In another aspect, a method of generating a library of novel AAV capsids is provided. Embodiments of this aspect include a method of isolating a recombinant AAV plasmid that includes a novel AAV capsid. These embodiments will now be discussed with reference to FIGS. 8-9.

Figure 8:
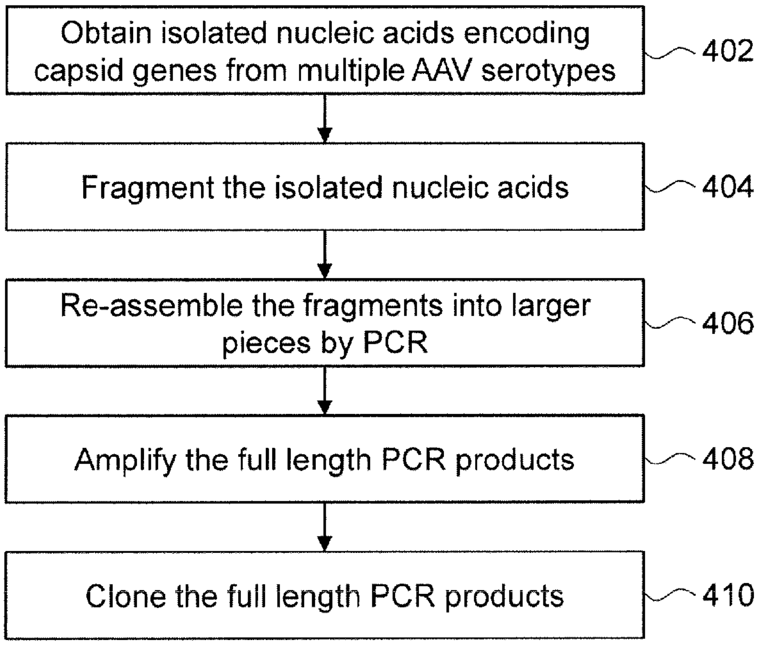
FIG. 8 is a flow chart summarizing a method of generating a library of AAV capsids.

FIG. 8 summarizes a method of generating a library of novel AAV capsids. As shown in step 402 of FIG. 8, isolated nucleic acids encoding capsid genes are obtained from multiple AAV serotypes (two or more) using primers designed to include a serotype-specific part fused with common signature regions that flank the capsid nucleic acid sequence. Then, as shown in step 404, the isolated nucleic acids are digested or fragmented, such as with DNAseI, into fragments of, for example, between about 0.2 and about 1.0 kb. The fragments are then re-assembled in step 406 into larger pieces by performing PCR, such as with Taq polymerase, in the absence of additional primers. Because of the related nature of the fragmented genes, the gene fragments have overlapping regions of homology that allow the fragments to self prime in the absence of additional primer. After multiple rounds of PCR, products having a length approximately equal to that of the originally capsid genes are obtained. The PCR products include hybrid products that contain capsid regions from multiple AAV serotypes.

As shown in step 408, the full length PCR products are then PCR amplified, preferably with Platinum Pfx polymerase, using primers that bind to the signature regions that are contained in the full length PCR products because they were present in the original primers used to isolate the capsid nucleic acid sequences. The PCR products from step 408 are then cloned into a conventional plasmid, as shown in step 410 to provide a library of novel AAV capsid genes. In one embodiment, the capsid genes are cloned into an ITR-rep-containing AAV plasmid, to subsequently create the actual viral library.

Figure 9:
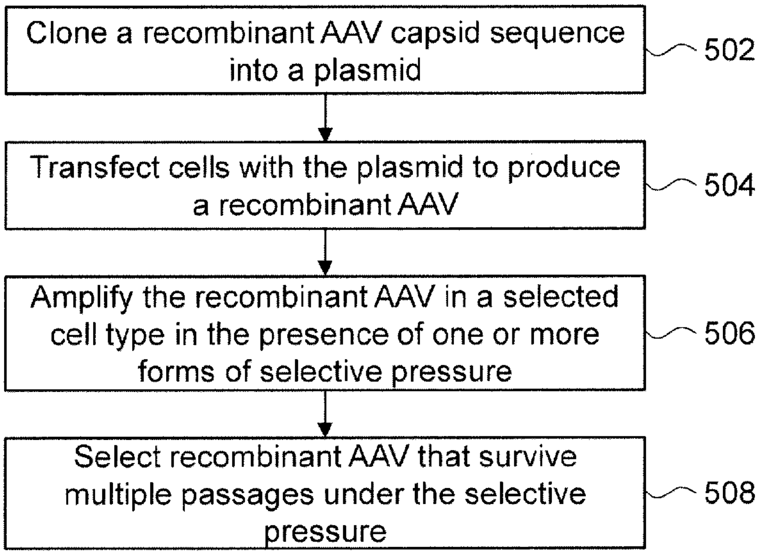
FIG. 9 is a flow chart summarizing a method of isolating recombinant AAV.

FIG. 9 summarizes a method of isolating a recombinant AAV that includes a novel recombinant AAV capsid, i.e., a “hybrid capsid” is isolated as described above with respect to FIG. 8. In step 502, hybrid capsid sequences are cloned into a plasmid that is capable of producing an infectious AAV genome, such as a plasmid comprising the AAV-2 rep gene, as well as the two AAV-2 ITRs. In step 504, the plasmid library is transfected into cells together with an adenoviral helper plasmid to produce virus. In step 506, the virus is then amplified in cells in the presence of a helpervirus, such as wildtype Adenovirus-5 helpervirus. The virus may be amplified in the presence of one or more forms of selective pressure, such as in the presence of human immune globulin. The viruses that survive multiple passages under the selective pressure are chosen for further study or use, as shown in step 508.

In a supporting study (Example 1), the approach outline in FIGS. 8-9 was used to generate a library. In brief, the capsid gene from eight different AAV serotypes (AAV-2, AAV-4. AAV-5, AAV-8, AAV-9, avian AAV, bovine AAV, and caprine AAV) was fragmented, and the PCR products from step 406 were blunt cloned into the pCR4-TOPO plasmid, available from Invitrogen. Twenty-four (24) subclones were sequenced to confirm that capsid sequences that are a hybrid of different serotypes were created. Sequences from all eight of the serotypes were represented in the subclones. Typically, the hybrid capsid sequences included sequences from at least two, and often, more than six, of the serotypes. The capsid sequences in the pCR4-TOPO plasmid were then subcloned into a plasmid comprising the AAV-2 rep gene, as well as the two AAV-2 ITRs, that was then used to transform bacteria. It is estimated that approximately a library of $3\times10^4$ hybrid AAV capsid gene variants were obtained from a single reaction and from 10 plates of bacteria. Up-scaling (including plating on 100 plates of bacteria) resulted in a plasmid library of approximately $6.9\times10^5$ clones. This plasmid library was then co-transfected into 293 human embryonic kidney cells together with an adenoviral helper plasmid, to produce a viral library of hybrid AAV particles.

This library of AAV capsid variants was then co-infected with wildtype Adenovirus-5 helpervirus and successfully amplified in several cell lines, including human kidney 293 cells, human hepatoma Huh-7 cells, and mouse fibroblast NIH3T3 cells. Successful amplification of the viral library was confirmed by Western blots of whole cell extracts using the B1 antibody which recognizes an eight amino acid epitope that is largely conserved over most known AAV serotypes, and thus should be present in the majority of the hybrid AAVs described herein. Replicating AAV particles were detected in all of the tested cell lines for up to five consecutive passages. Whole freeze-thaw cell extracts were used for infecting fresh cells each time. To date, the viral library has also been successfully passaged six times in primary human hepatocytes, which are notoriously difficult to infect with vectors based on wiidtype AAVs.

The viral library was also amplified in human Huh-7 cells in the presence of human immune globulin (IVIG). It was found that the specific IVIG used (IVIG Gamimune®N 10% from Bayer) contained abundant neutralizing antibodies against AAV-2 and AAV-3, as well as some antibodies against AAV-1, AAV-4, AAV-5, and AAV-6. Thus, amplification in human Huh-7 cells in the presence of IVIG provided a selective pressure for AAV hybrids comprising domains from different serotypes since selecting for a high efficiency infection of Huh-7 cells favors AAV-2 domains, while selecting for escape from IVIG neutralization favors AAV-8 and AAV-9 domains. The selection was successful, as it was found that with increasing passages of the library, an increasing tolerance to IVIG was achieved. After the fourth passage, surviving virus could be amplified in the presence of 500 μL IVIG, while after the first passage, surviving virus could only be amplified in the presence of approximately 10 μA IVIG.

After the 5$^{th}$ passage, the hybrid capsid sequences were PCR amplified and blunt cloned in pCR4-TOPO. The capsid sequences from 96 colonies were sequenced and found to be identical. The hybrid capsid sequence is the AAV-DJ sequence described above.

In summary, a plasmid library was created using DNA Family Shuffling (Crameri, et al., *Nature,* 391: 288-291 (1998)) of parental AAV capsid genes. Subsequently, a viral library was generated, by transfecting the plasmid library into cells together with an adenoviral helper plasmid. This second viral library was then subjected to selection pressure, to isolate specific candidates. From those, selected shuffled capsid genes were isolated and subcloned into an AAV helper plasmid, to make recombinant AAV vectors comprising the hybrid capsid. More particularly, DNA Family shuffling was used to create a complex library of hybrid particles from eight different wildtypes. Serial amplification on human cells enriched hybrids from a multitude of AAV serotypes, typically containing an AAV-2 heparin binding domain (HBD). More stringent selection with pooled human antisera yielded a single AAV-2-8-9 chimera, referred to herein as AAV-DJ. Recombinant AAV-DJ vectors were superior to natural AAVs in cultured cells and outperformed the AAV-2 prototype in tissue in vivo. Vectors with an AAV-DJ capsid were superior in vitro and gave a robust and specific in vivo performance, and provided an ability to evade humoral neutralization by human serum.

IV. Examples

The following examples are illustrative in nature and are in no way intended to be limiting.

Example 1

AAV Capsid Library Generation

A. Plasmids for AAV Capsid Library Generation

Plasmids containing full-length capsid (cap) genes of seven different AAV serotypes were obtained (AAV-2, -4, -5, -8, -9, avian and bovine AAV). Goat AAV was partly synthesized (GeneArt, Regensburg, Germany) as a 888 nt fragment (nt 1023 to 1910). This subclone spans the entire right half of the goat AAV capsid protein, which comprises all 42 reported differences between goat AAV and AAV-5. The other seven cap genes were initially amplified via PCR and subcloned into pBlueScript II SK (Stratagene). The purpose was to flank all cap genes with sites for the unique restriction enzymes Pac I (5') or Asc I (3'), to facilitate later cloning of "shuffled" cap genes into a wildtype AAV plasmid (see below). All primers also contained either a Hind III (5') or a Spe I (3') site, to allow directed cloning into pBlueScript (none of the four restriction enzymes cuts in any parental cap gene). A 20 nt signature region was inserted between the two restriction sites in each primer, to provide conserved primer binding sites for later PCR amplification of shuffled genes. Together, the sequence of the forward primers was 5' GGACTC AAGCTT GTCTGAGTGACTAGCATTCG TTAATTAA CAGGTATG 3' (SEQ ID NO:6; Hind III site in bold, Pac I site in italics/bold, signature region underlined) directly attached at the 3' end to the first 22 nt of each cap gene following its ATG start codon. Likewise, the reverse primer was 5' CGTGAG ACTAGT GCTTACTGAAGCTCACTGAG GGCGCGCC TTA 3' (SEQ ID NO:7; Spe I site in bold, Acs I site in italics/bold, signature region underlined) directly attached at the 3' end to the last 22 nt of each cap gene up to the TAA stop codon.

In parallel, a wildtype cap recipient plasmid was engineered to contain the AAV-2 packaging elements (ITRs) flanking the AAV-2 rep gene (encoding AAV replication proteins), together with Pac I and Asc I sites for cap cloning, and the AAV-2 polyadenylation site. Therefore, AAV-2 rep (nt 191 to 2189) was PCR amplified using primers containing Bgl II sites and then subcloned into pTRUF3 (carrying AAV-2 ITRs with adjacent Bgl II sites). The forward primer used was 5' CGAACC AGATCT GTCCTGTATTAGAGGTCACGTGAG 3' (SEQ ID NO:8; Bgl II site in bold, AAV-2 nt 191 underlined), and the reverse primer was 5' GGTAGC AGATCT GTTCGACCGCAGCCTTTCGAATGTCCGG TTTATT GATTA GGCGCGCC CTGGACTC TTAATTAA CATTTATTGTTCAAAGATGC 3' (SEQ ID NO:9; Bgl II site in bold, polyadenylation signal underlined, Asc I site in italics/bold, Pac I site in italics/bold/ underlined, AAV-2 rep stop codon in italics/underlined). Note that this changed the AAV-2 Swa I site (downstream of rep stop codon) into a Pac I site.

B. DNA Family Shuffling of AAV Capsid Genes

For DNA shuffling of AAV capsid genes, a 2-step protocol was used where the parental genes were first fragmented using DNase I enzyme and then reassembled into a full-length gene via primer-less PCR. This was followed by a second PCR including primers binding outside of the cap genes, allowing their subcloning into the wildtype recipient ITR/rep plasmid. Initially, all cap genes were isolated from the subclones via Hind III/Spe I digestion (Eco RI for goat AAV) and then reaction conditions were optimized as follows. Various DNAse I concentrations and incubation times were tested, aiming to obtain a pool of fragments between 0.2 and 1.0 kb in size. Optimal conditions found were: 1 μg per cap gene. 1 μL 1:200 pre-diluted DNase I (10 U/μL, Roche), 50 mM Tris Cl pH 7.4, 1 mM $MgCl_2$, total volume of 50 μL. The reaction was incubated for 2 min at room temperature and then stopped by heat inactivating at 80° C. for 10 min. Fragments of the desired sizes were isolated by running the entire reaction on a 1% agarose gel (total final volume ~60 μl). The re-assembly PCR reaction was then optimized by testing various DNA polymerases (Pfx Platinum, Stratagene; DeepVent, NEB; Taq, Amersham) and respective conditions. Best results were obtained using PuReTaq Ready-To-Go PCR Beads (Amersham) and the following conditions: 25 μL purified cap fragments, program: 4 min 95° C., 40 cycles (1 min 95° C., 1 min 50° C., 3 min 72° C.), 10 min 72° C., 10 min 4° C. Agarose gel (1%) analysis of 1 μL from this reaction typically showed a smear up to 5 kb and no distinct bands. The same three polymerases as above were then evaluated for the primer-containing second PCR, and the following conditions were found optimal: 1 μL Pfx Platinum, 2 μL product from first PCR, 1 mM MgSO4, 1 μg of each primer (see below), 0.3 mM each dNTP, total volume 50 μL, program: 5 min 94° C., 40 cycles (30 sec 94° C., 1 min 55° C., 3 minutes 68° C.), 10 min 68° C., 10 min 4° C. The primers used bound to the 20 nt signature regions described in the previous chapter. This reaction gave a distinct ~2.2 kb full-length cap band (1% agarose gel), which was purified (60 μL total) and cloned (4 μL) using the Zero Blunt TOPO PCR cloning kit (with electro-competent TOP10 cells) (Invitrogen, Carlsbad, Calif., USA). This intermediate cloning step significantly enhanced the yield of shuffled cap genes, as compared to efforts to directly clone the PCR product via conventional means (data not shown). The shuffled cap genes were then released from the TOPO plasmid via Pac I and Asc I double digestion and cloned into the appropriately digested ITR/rep recipient plasmid. Performing all these reactions under minimal conditions (volumes and amounts), a library of approximately $3\times10^4$ bacterial colonies was obtained. Up-scaling of each step (including final plating on 100×15 cm plates) resulted in a final library of ~$6.9\times10^5$ plasmid clones. Its integrity, genetic diversity and functionality was confirmed by DNA sequencing and small scale expression studies. From the latter, it was determined by extrapolation that the viral library (below) retained >90% viability.

C. Selective In Vitro Amplification of the Capsid Library

A viral library was prepared by transfecting 50× T225 flasks of 293 cells with 50 μg plasmid per flask from the bacterial library, together with 25 μg of an adenoviral helper plasmid. The resulting hybrid viruses were concentrated, purified and titrated as described for recombinant AAV. The final library had a particle titer (viral genomes) of $8.2\times10^{11}$/mL. Various amounts of purified shuffled AAV were then incubated with different cell lines (in 6 cm dishes), together with also varying amounts of helper Adenovirus type 5. Ideally, the Adenovirus would lyse the cells within three days, giving the AAV sufficient time to replicate. The AAV amounts were adjusted to obtain minimal signals in Western blot analyses of cell extracts. This helped to optimize the stringency of the library in each amplification round, by ensuring that a single viral genome was delivered to each cell, and subsequently packaged into the capsid expressed from its own genome.

In one set of experiments, the library was additionally subjected to IVIG pressure during amplification. Therefore, various volumes of the library and IVIG (Gamimune®N 10%, Bayer, Elkhardt, Ind., USA) were mixed and incubated for 1 hour at 37° C., and then added to the cells. After overnight incubation, the cells were washed and super-infected with Adenovirus. The wash step was included to avoid helper virus inactivation by the IVIG. As before. AAV amplification was controlled by Western blotting after each round, and only supernatants giving minimal expression were used for subsequent infections. The increasing IVIG resistance of the library during consecutive passages allowed continuous escalation of the IVIG doses. All amplification experiments comprised five infection cycles (Adenovirus was heat inactivated between each and then added fresh, to avoid uncontrolled amplification). Finally, viral DNA was purified from the supernatant (DNA Extractor Kit, Wako, Japan), and AAV cap genes were PCR amplified (DeepVent Polymerase), using primers 5' GATCTGGTCAATGTGGATTTGGATG 3' (SEQ ID NO:10; binding in AAV-2 rep upstream of the Pac I site used for cap cloning) and 5' GACCGCAGCCTTTCGAATGTCCG 3' (SEQ ID NO:11; binding downstream of the Asc I site and polyadenylation signal). The resulting blunt-ended cap genes were subcloned using the Zero Blunt TOPO PCR cloning kit for Sequencing (Invitrogen) and DNA was prepared from individual clones (96 per cell line/amplification round).

To assemble full-length cap sequences, T3 and T7 primers were used to obtain the 5' and 3' ends of each clone, and then individual primers (not shown) were designed to acquire the remaining sequence. Alignments (DNA and protein) with the eight parental cap genes were performed using BLAST and Vector NTI 10/AlignX software (Invitrogen).

D. AAV Protein Analyses

Western blot and immunofluorescence analyses were carried out as reported (Grimm, D. et al., *Blood,* 102:2412-2419 (2003)) using the monoclonal B1 antibody for detection of immobilized AAV capsid proteins, useful because its eight amino acid epitope is largely conserved-across known AAV serotypes.

Example 2

In Vitro Transduction with Recombinant AAV-DJ Vectors

A. Helper Plasmid Cloning and Vector Particle Production

Helper plasmids expressing wildtype AAV-2, -8 or -9 cap together with AAV-2 rep genes, as well as AAV-2-based vector plasmids expressing the hFIX gene from a liver-specific or the EF1α promoter, were previously described (Nakai, H. et al., *J. Virol.,* 79:214-224 (2005)); Gao, G. et al., *J. Virol.,* 78:6381-6388 (2004)). Two self-complementary vector plasmids expressing either the gfp gene from a CMV promoter, or the hAAT gene from an RSV (Rous Sarcoma Virus) promoter, were prepared using conventional techniques.

For cloning of helper plasmids expressing shuffled cap genes, the entire AAV-8 cap gene was removed from the AAV-8 helper construct by cutting with Swa I and Pme I (both create blunt ends; Swa I cuts 9 nt upstream of the VP1 start codon, Pme I cuts 53 nt downstream of the polyadenylation signal). The novel cap genes were amplified from the respective TOPO constructs (see above) via PCR, using the forward primer 5' AAAT CAGGT 3' (SEQ ID NO:12; the underlined nt restored the Swa I site to maintain correct reading frames) directly attached at the 3' end to the first 25 nt of each cap gene, which for AAV-DJ was: ATGGCTGCCGATGGTTATCTTCCAG (SEQ ID NO:13; identical in AAV-2, -8 and -9). The reverse primer was 5' AAAC AATTCGCCCTTCGCAGAGACCAAAGTTCAACTGAAACGAATCAACCGG TTTATT GATTAACAGGCAA 3' (SEQ ID NO:14; nt restoring the Pme I site are underlined, the polyadenylation signal is shown in bold) directly attached at the 3' end to the last (3') 23 nt of the shuffled capsid genes, which for AAV-DJ was: TTACAGATTACGGGTGAGGTAAC, 3'-5' orientation, SEQ ID NO:15). PCRs were performed using DeepVent DNA Polymerase (NEB), creating blunt ends allowing straight-forward insertion into the linearized AAV-8 helper plasmid. Insert junctions and correct orientation were confirmed via DNA sequencing (Biotech Core). Vector production and particle titration (dot blot) were performed as previously described (Nakai, H. et al., *J. Virol.,* 79:214-224 (2005)). Yields for all vectors including AAV-DJ and the HBD mutants typically exceeded $6\times10^{13}$ total physical particles per 50× T225 flasks ($2\times10^9$ cells).

B. In Vitro Transduction

All transformed cell lines were maintained in DMEM (Gibco) containing 10% fetal calf serum, 2 mM L-glutamine and 50 IU/ml of each penicillin and streptomycin at 37° C. in 5% $CO_2$. Fresh primary human hepatocytes (in 6-well plates without Matrigel) were obtained from Admet (Durham, N.C., USA) and maintained in Hepatocyte Basal Medium (Cambrex, Walkersville, Md., USA) with recommended supplements. Titration of gfp-expressing recombinant AAV particles was performed in 96-well plates, following normalization of each virus stock to $2\times10^9$ particles/mL. For in vitro neutralization studies, 50 μL per vector preparation were incubated with serial 10-fold dilutions of two batches of IVIG (designated IVIG1 and IVIG2) or mouse sera (following a 1 hour heat inactivation at 56° C.) for 1 hour at 37° C. prior to titration on cells. Titers of neutralizing antibodies were calculated as reported (Grimm, D. et al., *Blood,* 102: 2412-2419 (2003)).

Example 3

In Vivo Studies

Recombinant AAVs with either the AAV-DJ, AAV-2, AAV-8, or AAV-9 capsids were produced by triple transfecting cells with a plasmid encoding the human factor IX (FIX) gene under the control of an adjacent liver-specific promoter and flanked by AAV inverted terminal repeats (ITRs), a plasmid encoding adenoviral helper genes, and a plasmid encoding the AAV-2 rep gene and either the AAV-DJ, AAV-2, AAV-8, or AAV-9 capsid protein. The liver-specific promoter that was used was a human alpha-1-antitrypsin (hAAT) promoter fused with an apolipoprotein E (ApoE) enhancer and an HCR (hepatic locus control region). The AAV ITRs that were used were derived from AAV-2 and are identical to each other.

Doses of $5\times10^{10}$, $2\times10^{11}$, and $1\times10^{12}$ (low, medium, and high, respectively) recombinant viral particles were injected into mice via tail vein infusions with a volume of 300 microliters infused over a period of about 10 seconds. The mice were bled at 1, 3, and 8 days after the infusions. The FIX protein plasma levels were quantified by ELISA, and the results are shown in FIG. 4.

Example 4

In Vivo Studies

A. Expression Studies in Mice

Wildtype female C57/BL6 mice (6 to 8 weeks old, 20 to 25 grams) were purchased from Jackson Laboratory (Bar Harbor, Me., USA). Recombinant AAV expressing the hFIX or hAAT genes were administered in 300 μL 1×PBS via tail vein infusion. Blood was collected at the indicated timepoints via retroorbital bleeding, and plasma hFIX or hAAT levels were determined via ELISA as previously described (Nakai, H. et al., *J. Virol.,* 79:214-224 (2005); Grimm, D. et al., *Nature,* 441:537-541 (2006)). Results for the hAAT-expressing vectors are shown in FIG. 5.

Genomic DNA was extracted from mouse tissues and analyzed via Southern blotting, using hFIX- or hAAT-specific probes, as previously reported (Nakai, H. et al., *J. Virol.,* 76:11343-11349 (2002)).

B. Immunologic In Vivo Assays

For passive immunization studies, mice (n=4 per group) were injected intravenously (tail vein) with 40 μL (low dose) or 200 μL (high dose) of IVIG (100 mg/mL) diluted in 1×PBS to a total volume of 300 μL, and 24 hours later infused (tail vein) with $2\times10^{11}$ recombinant hFIX-expressing AAV. Plasma hFIX levels per virus and timepoint are shown in FIGS. 6A-6B as percent of corresponding levels in control mice (PBS instead of IVIG).

For cross-neutralization studies, mice were immunized against individual AAV serotypes by peripheral infusion of $1\times10^{11}$ recombinant hAAT-expressing particles. Three weeks later, mouse serum was collected for in vitro neutralization assays, before the mice were re-infused with $1\times10^{11}$ ($5\times10^{11}$ for AAV-2) recombinant hFIX-expressing AAV. Sera was taken from the mice at the time of re-injection (H), as well as from a parallel group of mice injected with a lower dose (L) of $2\times10^{10}$ particles. Neutralizing antibody titers (NAb) against the wildtype AAVs or AAV-DJ were determined. Results are shown in FIGS. 6C-6D.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

SEQUENCE LISTING

```
<160> NUMBER OF SEQ ID NOS: 15

<210> SEQ ID NO 1
<211> LENGTH: 737
<212> TYPE: PRT
<213> ORGANISM: Artificial Sequence
```

-continued

<220> FEATURE:
<223> OTHER INFORMATION: Synthetic capsid protein

<400> SEQUENCE: 1

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
            180                 185                 190

Ala Ala Pro Ser Gly Val Gly Ser Leu Thr Met Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400
```

-continued

```
Pro Ser Gln Met Leu Lys Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Thr Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Ser Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Gln Ser Gly Val Leu Ile Phe
    530                 535                 540

Gly Lys Gln Gly Ser Glu Lys Thr Asn Val Asp Ile Glu Lys Val Met
545                 550                 555                 560

Ile Thr Asp Glu Glu Glu Ile Arg Thr Thr Asn Pro Val Ala Thr Glu
                565                 570                 575

Gln Tyr Gly Ser Val Ser Thr Asn Leu Gln Arg Gly Asn Arg Gln Ala
            580                 585                 590

Ala Thr Ala Asp Val Asn Thr Gln Gly Val Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 2
<211> LENGTH: 2215
<212> TYPE: DNA
<213> ORGANISM: Artificial Sequence
<220> FEATURE:
<223> OTHER INFORMATION: Synthetic capsid protein encoding sequence

<400> SEQUENCE: 2

```
atggctgccg atggttatct tccagattgg ctcgaggaca ctctctctga aggaataaga      60

cagtggtgga agctcaaacc tggcccacca ccaccaaagc ccgcagagcg gcataaggac     120

gacagcaggg gtcttgtgct tcctgggtac aagtacctcg gacccttcaa cggactcgac     180
```

```
aagggagagc cggtcaacga ggcagacgcc gcggccctcg agcacgacaa agcctacgac    240
cggcagctcg acagcggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcactctcct gtggagccag actcctcctc gggaaccgga    480
aaggcgggcc agcagcctgc aagaaaaaga ttgaattttg gtcagactgg agacgcagac    540
tcagtcccag accctcaacc aatcggagaa cctcccgcag ccccctcagg tgtgggatct    600
cttacaatgg ctgcaggcgg tggcgcacca atggcagaca ataacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caagcaaatc    780
tccaacagca catctggagg atcttcaaat gacaacgcct acttcggcta cagcaccccc    840
tgggggtatt ttgactttaa cagattccac tgccactttt caccacgtga ctggcagcga    900
ctcatcaaca acaactgggg attccggccc aagagactca gcttcaagct cttcaacatc    960
caggtcaagg aggtcacgca gaatgaaggc accaagacca tcgccaataa cctcaccagc   1020
accatccagg tgtttacgga ctcggagtac cagctgccgt acgttctcgg ctctgcccac   1080
cagggctgcc tgcctccgtt cccggcggac gtgttcatga ttccccagta cggctaccta   1140
acactcaaca acggtagtca ggccgtggga cgctcctcct tctactgcct ggaatacttt   1200
ccttcgcaga tgctgagaac cggcaacaac ttccagttta cttacacctt cgaggacgtg   1260
cctttccaca gcagctacgc ccacagccag agcttggacc ggctgatgaa tcctctgatt   1320
gaccagtacc tgtactactt gtctcggact caaacaacag gaggcacgac aaatacgcag   1380
actctgggct tcagccaagg tggccctaat acaatggcca atcaggcaaa gaactggctg   1440
ccaggaccct gttaccgcca gcagcgagta tcaaagacat ctgcggataa caacaacagt   1500
gaatactcgt ggactggagc taccaagtac cacctcaatg gcagagactc tctggtgaat   1560
ccgggcccgg ccatggcaag ccacaaggac gatgaagaaa agtttttttc ctcagagcgg   1620
ggttctcatc tttgggaagc aaggctcaga gaaaacaaat gtggacattg aaaaggtcat   1680
gattacagac gaagaggaaa tcaggacaac caatcccgtg gctacggagc agtatggttc   1740
tgtatctacc aacctccaga gaggcaacag acaagcagct accgcagatg tcaacacaca   1800
aggcgttctt ccaggcatgg tctggcagga cagagatgtg taccttcagg ggcccatctg   1860
ggcaaagatt ccacacacgg acggacattt tcacccctct cccctcatgg gtggattcgg   1920
acttaaacac cctccgcctc agatcctgat caagaacacg cctgtacctg cggatcctcc   1980
gaccaccttc aaccagtcaa agctgaactc tttcatcacc cagtattcta ctggccaagt   2040
cagcgtggag atcgagtggg agctgcagaa ggaaaacagc aagcgctgga accccgagat   2100
ccagtacacc tccaactact acaaatctac aagtgtggac tttgctgtta atacagaagg   2160
cgtgtactct gaaccccgcc ccattggcac ccgttacctc acccgtaatc tgtaa        2215
```

<210> SEQ ID NO 3
<211> LENGTH: 735
<212> TYPE: PRT
<213> ORGANISM: Adeno-associated virus 2

<400> SEQUENCE: 3

```
Met Ala Ala Asp Gly Tyr Leu Pro Asp Trp Leu Glu Asp Thr Leu Ser
 1               5                  10                  15
```

-continued

```
Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445
```

```
Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Arg Gly Leu Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 4
<211> LENGTH: 738
<212> TYPE: PRT
<213> ORGANISM: Adeno-associated virus 8

<400> SEQUENCE: 4

Met Ala Ala Asp Gly Tyr Leu Pro Asp Trp Leu Glu Asp Asn Leu Ser
 1               5                  10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95
```

-continued

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
```

```
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 5
<211> LENGTH: 736
<212> TYPE: PRT
<213> ORGANISM: Adeno-associated virus 9

<400> SEQUENCE: 5

Met Ala Ala Asp Gly Tyr Leu Pro Asp Trp Leu Glu Asp Asn Leu Ser
 1               5                  10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160
```

-continued

```
Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
```

-continued

```
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6

ggactcaagc ttgtctgagt gactagcatt cgttaattaa caggtatg                48


<210> SEQ ID NO 7
<211> LENGTH: 43
<212> TYPE: DNA
<213> ORGANISM: Artificial Sequence
<220> FEATURE:
<223> OTHER INFORMATION: Primer

<400> SEQUENCE: 7

cgtgagacta gtgcttactg aagctcactg agggcgcgcc tta                     43


<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8

cgaaccagat ctgtcctgta ttagaggtca cgtgag                             36


<210> SEQ ID NO 9
<211> LENGTH: 95
<212> TYPE: DNA
<213> ORGANISM: Artificial Sequence
<220> FEATURE:
<223> OTHER INFORMATION: Primer

<400> SEQUENCE: 9

ggtagcagat ctgttcgacc gcagcctttc gaatgtccgg tttattgatt aggcgcgccc   60

tggactctta attaacattt attgttcaaa gatgc                              95
```

-continued

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
gatctggtca atgtggattt ggatg 25

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gaccgcagcc tttcgaatgt ccg 23

<210> SEQ ID NO 12
<211> LENGTH: 9
<212> TYPE: DNA
<213> ORGANISM: Artificial Sequence
<220> FEATURE:
<223> OTHER INFORMATION: Primer

<400> SEQUENCE: 12 aaatcaggt 9

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
atggctgccg atggttatct tccag 25

<210> SEQ ID NO 14
<211> LENGTH: 71
<212> TYPE: DNA
<213> ORGANISM: Artificial Sequence
<220> FEATURE:
<223> OTHER INFORMATION: Primer

<400> SEQUENCE: 14
aaacaattcg cccttcgcag agaccaaagt tcaactgaaa cgaatcaacc ggtttattga 60
ttaacaggca a 71

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
ttacagatta cgggtgaggt aac 23

What is claimed is:

1. In a method of screening an AAV viral library comprising hybrid full-length capsid genes prepared by:

(i) isolating AAV capsid nucleotide sequences from two or more AAV serotypes;

(ii) digesting the AAV capsid nucleotide sequences into fragments;

(iii) reassembling the fragments into a full-length gene using primer-less PCR to form PCR products;

(iv) cloning the re-assembled PCR products into plasmids to generate a library of recombinant AAV plasmids, an improvement for increasing infectivity of an AAV virion and enhancing resistance to neutralization by anti-AAV antibodies, said improvement comprising:

(a) transfecting mammalian cells with the library of recombinant AAV plasmids from step (iv);

(b) incubating the transfected cells in the presence of anti-AAV antibodies until the cells lyse to produce an amplified and packaged AAV viral library; and (c) passaging the AAV viral library in mammalian cells in the presence of anti-AAV antibodies and selecting an AAV virion that survives said passaging, wherein the selected AAV virion has increased infectivity and enhanced resistance to neutralization by anti-AAV antibodies, relative to wildtype AAV-2.

2. The improvement of claim 1, wherein isolating includes isolating AAV capsid nucleotide sequences from human AAV serotypes and non-human AAV serotypes.

3. The improvement of claim 2, wherein isolating includes isolating AAV capsid nucleotide sequences selected from the group consisting of AAV-2, AAV-8, and AAV-9.

4. The improvement of claim 1, wherein said transfecting comprises transfecting into 293 kidney cells with a helper virus.

5. The improvement of claim 1, wherein said anti-AAV antibodies comprise human anti-AAV antibodies.

6. A recombinant AAV (rAAV) library prepared according to the improvement of claim 1.

* * * * *

UNITED STATES PATENT AND TRADEMARK OFFICE

CERTIFICATE OF CORRECTION

PATENT NO. : 8,574,583 B2
APPLICATION NO. : 13/297110
DATED : November 5, 2013
INVENTOR(S) : Kay et al.

It is certified that error appears in the above-identified patent and that said Letters Patent is hereby corrected as shown below:

In the Specification

Column 23, Lines 42-52 should read:
<210> SEQ ID NO 2
<211> LENGTH: 2214
<212> TYPE DNA
<213> ORGANISM: Artificial Sequence
<220> FEATURE:
<223> OTHER INFORMATION: Synthetic capsid protein encoding sequence <400>SEQUENCE: 2
atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tcctgggtac aagtacctcg gacccttcaa cggactcgac 180
aagggagagc cggtcaacga ggcagacgcc gcggccctcg agcacgacaa agcctacgac 240

Column 25, Lines 1-33 should read:
cggcagctcg acagcggaga caacccgtac ctcaagtaca accacgccga cgccgagttc 300
caggagcggc tcaaagaaga tacgtctttt gggggcaacc tcgggcgagc agtcttccag 360
gccaaaaaga ggcttcttga acctcttggt ctggttgagg aagcggctaa gacggctcct 420
ggaaagaaga ggcctgtaga gcactctcct gtggagccag actcctcctc gggaaccgga 480
aaggcgggcc agcagcctgc aagaaaaaga ttgaattttg gtcagactgg agacgcagac 540
tcagtcccag accctcaacc aatcggagaa cctcccgcag ccccctcagg tgtgggatct 600
cttacaatgg ctgcaggcgg tggcgcacca atggcagaca ataacgaggg cgccgacgga 660
gtgggtaatt cctcgggaaa ttggcattgc gattccacat ggatgggcga cagagtcatc 720
accaccagca cccgaacctg ggccctgccc acctacaaca accacctcta caagcaaatc 780
tccaacagca catctggagg atcttcaaat gacaacgcct acttcggcta cagcaccccc 840
tgggggtatt ttgactttaa cagattccac tgccactttt caccacgtga ctggcagcga 900
ctcatcaaca acaactgggg attccggccc aagagactca gcttcaagct cttcaacatc 960

Signed and Sealed this
Twenty-ninth Day of December, 2020

Andrei Iancu
*Director of the United States Patent and Trademark Office* caggtcaagg aggtcacgca gaatgaaggc accaagacca tcgccaataa cctcaccagc 1020
accatccagg tgtttacgga ctcggagtac cagctgccgt acgttctcgg ctctgcccac 1080
cagggctgcc tgcctccgtt cccggcggac gtgttcatga ttccccagta cggctaccta 1140
acactcaaca acggtagtca ggccgtggga cgctcctcct tctactgcct ggaatacttt 1200
ccttcgcaga tgctgagaac cggcaacaac ttccagttta cttacacctt cgaggacgtg 1260
cctttccaca gcagctacgc ccacagccag agcttggacc ggctgatgaa tcctctgatt 1320
gaccagtacc tgtactactt gtctcggact caaacaacag gaggcacgac aaatacgcag 1380
actctgggct tcagccaagg tgggcctaat acaatggcca atcaggcaaa gaactggctg 1440
ccaggaccct gttaccgcca gcagcgagta tcaaagacat ctgcggataa caacaacagt 1500
gaatactcgt ggactggagc taccaagtac cacctcaatg gcagagactc tctggtgaat 1560
ccgggcccgg ccatggcaag ccacaaggac gatgaagaaa agttttttcc tcagagcggg 1620
gttctcatct ttgggaagca aggctcagag aaaacaaatg tggacattga aaaggtcatg 1680
attacagacg aagaggaaat caggacaacc aatcccgtgg ctacggagca gtatggttct 1740
gtatctacca acctccagag aggcaacaga caagcagcta ccgcagatgt caacacacaa 1800
ggcgttcttc caggcatggt ctggcaggac agagatgtgt accttcaggg gcccatctgg 1860
gcaaagattc cacacacgga cggacatttt cacccctctc ccctcatggg tggattcgga 1920
cttaaacacc ctccgcctca gatcctgatc aagaacacgc ctgtacctgc ggatcctccg 1980
accaccttca accagtcaaa gctgaactct ttcatcaccc agtattctac tggccaagtc 2040
agcgtggaga tcgagtggga gctgcagaag gaaaacagca agcgctggaa ccccgagatc 2100
cagtacacct ccaactacta caaatctaca agtgtggact ttgctgttaa tacagaaggc 2160
gtgtactctg aaccccgccc cattggcacc cgttacctca cccgtaatct gtaa 2214